US011919857B2

(12) United States Patent
Liu et al.

(10) Patent No.: US 11,919,857 B2
(45) Date of Patent: Mar. 5, 2024

(54) PHTHALIDE DERIVATIVE, PREPARATION METHOD AND USE THEREOF

(71) Applicant: LANZHOU INSTITUTE OF CHEMICAL PHYSICS, CHINESE ACADEMY OF SCIENCES, Lanzhou (CN)

(72) Inventors: Junxi Liu, Lanzhou (CN); Yaming Zhang, Lanzhou (CN)

(73) Assignee: LANZHOU INSTITUTE OF CHEMICAL PHYSICS, CHINESE ACADEMY OF SCIENCES, Lanzhou (CN)

( * ) Notice: Subject to any disclaimer, the term of this patent is extended or adjusted under 35 U.S.C. 154(b) by 675 days.

(21) Appl. No.: 17/257,736

(22) PCT Filed: Jan. 17, 2019

(86) PCT No.: PCT/CN2019/072178
§ 371 (c)(1),
(2) Date: Jan. 4, 2021

(87) PCT Pub. No.: WO2020/007031
PCT Pub. Date: Jan. 9, 2020

(65) Prior Publication Data
US 2021/0276953 A1 Sep. 9, 2021

(30) Foreign Application Priority Data
Jul. 5, 2018 (CN) .......................... 201810730744.7

(51) Int. Cl.
C07D 209/48 (2006.01)
A61P 9/00 (2006.01)
A61P 39/06 (2006.01)

(52) U.S. Cl.
CPC .............. *C07D 209/48* (2013.01); *A61P 9/00* (2018.01); *A61P 39/06* (2018.01); *C07B 2200/07* (2013.01)

(58) Field of Classification Search
CPC .................................................. C07D 209/48
See application file for complete search history.

(56) References Cited

U.S. PATENT DOCUMENTS 3,959,269 A   5/1976   Houlihan et al.

FOREIGN PATENT DOCUMENTS

| CN | 109053546 A | 12/2018 |
| WO | WO 2006024837 A1 | 3/2006 |
| WO | 2017/174620 A1 | 10/2017 |

OTHER PUBLICATIONS

Malancona S. et al., "Identification of MK-5710 ((8aS)-8a-Methyl-1,3-Dioxo-2-[(1S,2R)-2-Phenylcy-Clopropyl]-N-(1-Phenyl-1H-Pyrazol-5-yl)Hexahydroimid azo[1,5-a]Pyrazine-7(1H)-Carboxamide), a Potent Smoothened Antagonist for Use in Hedgehog Pathway Dependent Malignancies, Part 1", Bioorganic & Medicinal Chemistry Letters 21:4422-4428 (2011).
European Extended Supplementary Search Report dated Dec. 8, 2021 received in European Application No. 19 83 0370.3.
Kinghorn A.D. et al., "Progress in the Chemistry of Organic Natural Products", vol. 104, p. 127, Springer International (2017).
Kuang X. et al., "Neuroprotective Role of Z-Ligustilide Against Forebrain Ischemic Injury in ICR Mice", Brain Research 1102(1):145-153 (2006).
Peng H-Y et al., "Neuroprotective Effect of Z-Ligustilide Against Permanent Focal Ischemic Damage in Rats", Biol. Pharm. Bull. 30(2):309-312 (Feb. 2007).
Qi H. et al., "Potential Roles of PI3K/Akt and Nrf2-Keap1 Pathways in Regulating Hormesis of Z-Ligustilide in PC12 Cells Against Oxygen and Glucose Deprivation", Neuropharmacology 62(4):1659-1670 (Nov. 2011).
Su Y-W et al., "Ligustilide Prevents LPS-Induced iNOS Expression in RAW 264.7 Macrophages by Preventing ROS Production and Down-Regulating the MAPK, NF-KB and AP-1 Signaling Pathways", Iternational Immunopharmacology 11(9):1166-1172 (2011).
Xu W. et al., "Protection Against B-Amyloid-Induced Neurotoxicity by Naturally Occurring Z-Ligustilide Through the Concurrent Regulation of p38 and PI3-K/Akt Pathways", Neurochemistry International 100:44-51 (2016).
Yanxia Z. et al., "Effect of Volatile Oil of the Angelica on the Proliferation and Apoptosis of Human Lung Adenocarcinoma Cell SPC-A-1", China Academic Journal 32(6):105-108 (2016), together with an English-language abstract.
Yu Y. et al., "Protection Against Hydrogen Peroxide-Induced Injury by Z-Ligustilide in PC12 Cells", Exp Brain Res 184(3):307-312 (2008).
Wu J. et al., "Synthesis and In Vitro Antiplatelet Aggregation Activity of Isosorbide Mononitrate-Based 3-n-Butylphthalide Derivatives", Chinese Journal of Medicinal Chemistry 22(6):483-489 (Dec. 2012), together with an English-language abstract.
Zuo A-H et al., "Research Progress Studies on Pharmacology and Pharmacokinetics of Ligustilide", China Journal of Chinese Materia Medica 37(22):3350-3353 (Nov. 2012), together with an English-language abstract.
International Search Report dated Apr. 19, 2019 issued in PCT/CN2019/072178.
Beck, J.J. et al. "Addition of Methyl Thioglycolate and Benzylamine to (Z)-Ligustilide, a Bioactfve Unsaturated Lactone Constituent of Several Herbal Medicines. An Improved Synthesis of (Z)-Ligustilide", Journal of Natural Products (Jul. 30, 1995), vol. 58, No. 7, pp. 1047-1055.

*Primary Examiner* — Laura L Stockton
(74) *Attorney, Agent, or Firm* — Scully, Scott, Murphy & Presser, P.C.

(57) ABSTRACT

The present invention discloses a phthalide derivative, the structure of said derivative is represented by Formula (I) or Formula (II). The present invention also discloses the preparation method and use of said derivative. The phthalide compound obtained through structure modifications in the present invention enhances the chemical stability and pharmacological activity of the phthalide compound, facilitating the improvement of the druggability of such compounds.

10 Claims, 10 Drawing Sheets

PHTHALIDE DERIVATIVE, PREPARATION METHOD AND USE THEREOF

TECHNICAL FIELD

The present invention belongs to the field of organic synthesis chemistry, and relates to a phthalide derivative as well as preparation method and use thereof.

BACKGROUND

In nature, the plants belonging to *Angelica* and *Ligusticum* in *Umbelliferae* all contain phthalide compounds, such as *Angelica sinensis* and *Ligusticum wallichii* as medicinal plants. These compounds constitute the main components of plant volatile oils, and most of them have a strong aromatic odor. They are rich in the plants, and have various compound structures. These compounds are generally chemically unstable, and are easily oxidized or degraded when they are alone and exposed to light, heat, and enzymes in the environment. However, these compounds generally have good pharmacological activities, such as anti-oxidation, anti-platelet aggregation, promotion of microcirculation, analgesic and anti-inflammatory effects, central nerve protection, and anti-tumor effects and other significant pharmacological activities.

Ligustilide is the main pharmacologically active ingredient in the volatile oils of umbelliferous plants such as *Angelica sinensis*, *Ligusticum wallichii* and other traditional Chinese medicines. Its content is up to approximately 1%, and it has significant cardiovascular and cerebrovascular pharmacological activities. A number of researches on the pharmacological activity of ligustilide have been conducted and is being conducted by domestic and foreign researchers, and related research results on pharmacological activity have been published, for example the important pharmacological activities of ligustilide in the central nerve protection, promotion of microcirculation, vasodilatation, inhibition of vascular smooth muscle cell proliferation, antidepressant effects, effects against Alzheimer's disease, and analgesic and anti-inflammatory effects. At the same time, researchers provide a large number of reviews for the pharmacological research results of ligustilide (A. Douglas Kinghorn, Heinz Falk, Simon Gibbons, and Jun'ichi Kobayashi edited, Progress in the Chemistry of Organic Natural Products, 2017, P127, Springer International Published; ZUO Ai-hua, WANG Li, XIAO Hong-bin, Research progress studies on pharmacology and pharmacokinetics of ligustilide, China Journal of Chinese Materia Medica, 2012, 37(22): 3350-3353).

Ligustilide can significantly reduce the cerebral infarction volume caused by cerebral ischemia-reperfusion, improve cerebral nerve functions, and reduce damage to cortical neuron and hippocampal neuron cells in rats. In order to further clarify the underlying mechanism of neuroprotection, X Kuang et al. and HY Peng et al. studied the transient and persistent cerebral ischemia-reperfusion models, respectively. The results show that ligustilide reduces the content of malondialdehyde in ischemic cerebral tissues in a dose-dependent manner, increases the activities of glutathione peroxidase and superoxide dismutase, enhances the expression of Bcl-2 and decrease the expression of Bax as well as the immunological activity of Caspase-3 enzyme. It is revealed that ligustilide plays a neuroprotective role in the injury caused by transient and persistent cerebral ischemia-reperfusion through antioxidant and anti-apoptotic mechanism. On this basis, the study of cognitive impairment, biochemical changes, and histopathological characteristics caused by chronic cerebral ischemia-reperfusion also shows that the protective effect of ligustilide on cognitive impairment and brain damage is achieved through anti-oxidation and increase of choline-like functional activity (X Kuang, Y Yao, J. R. Du, Y. X. Liu, C Y Wang, Z M Qian, Neuroprotective role of Z-ligustilide against forebrain ischemic injury in ICR mice, Brain Research, 2006, 1102(1): 145-153; Haiyan Peng, Junrong Du, Guangyi Zhang, Xi Kuang, Yanxin Liu, Zhongming Qian, and Chenyuan Wang, Neuroprotective effect of Z-Ligustilide against permanent focal ischemic damage in rats, Biol Pharm Bull, 2007, 30(2): 309-312). Ligustilide plays a neuroprotective role in $H_2O_2$-induced injury of PC12 cells by improving the antioxidant capacity of cell and inhibiting mitochondrial apoptosis pathway (Yan Yu, Junrong Du, Chenyuan Wang, Zhongming Qian, Protection against hydrogen peroxide-induced injury by Z-ligustilide in PC12 cells, Exp Brain Res, 2008, 184(3): 307-312). HY Qi et al. further studies the biphasic toxicant excitatory regulation effect of ligustilide in PC12 cells with oxygen-glucose deprivation. It not only can cause oxidative stress response through ROS generation and glutathione consumption, but also can activate the pro-survival signal through the interaction of PI3K and Nrf2 pathways, so that ligustilide can have pre-protection effects on PC12 cells under both low and high oxygen-glucose deprivation environments (Hongyi Qi, Yifan Han, Jianhui Rong, Potential roles of PI3K/Akt and Nrf2-Keap1 pathways in regulating hormesis of Z-ligustilide in PC12 cells against oxygen and glucose deprivation, Neuropharmacology, 2012, 62(4): 1659-1670). Ligustilide significantly improves the neurological function in the ischemia-reperfusion rat, significantly reducing the protein expression of the inflammatory factor NF-κB while reducing the infarct volume. Moreover, it can inhibit the inflammatory mediators induced by LPS in neuroglia cells (such as TNF-α, NO, IL-1α, MCP-1), and can improve the cognitive impairment and neuropathological symptoms caused by α-amyloid polypeptides by regulating NF-κB pathway, showing that ligustilide can play an anti-inflammatory effect by inhibiting NF-κB pathway. In addition, ligustilide can also inhibit the LPS-induced inflammatory response in RAW 264.7 by inhibiting ROS production and down-regulating MAPK, NF-κB, and AP-1 signaling pathways. In short, ligustilide can also play a neuroprotective role through the anti-inflammatory mechanism, which contributes to the treatment of neuroinflammatory diseases (Yuwen Su, Wenfei Chiou, Shiouhuei Chao, Menghwan Lee, Chienchih Chen, Yingchieh Tsai, Ligustilide prevents LPS-induced iNOS expression in RAW 264.7 macrophages by preventing ROS production and down-regulating the MAPK, NF-κB and AP-1 signaling pathways, International Immunopharmacology, 2011, 11(9): 1166-1172).

At a concentration of 1-30 μM, ligustilide inhibits β-amyloid-induced neurotoxicity through p38 and PI3K/Akt signaling pathways, supporting the therapeutical effect of ligustilide on Alzheimer's disease (AD) (Wei Xu, Li Yang, Ji Li, Protection against β-amyloid-induced neurotoxicity by naturally occurring Z-ligustilide through the concurrent regulation of p38 and PI3-K/Akt pathways, Neurochemistry International, 2016, 100: 44-51). Domestic and foreign relevant literatures show that ligustilide has a significant pharmacological activity.

The phthalide compounds are classified into a benzene ring type (such as n-butenylphthalide), a dihydrobenzene ring type (such as ligustilide), or a tetrahydrobenzene ring type (such as senkyunolide H) according to the degree of hydrogenation reduction of six-membered ring. Meanwhile, the side chain and benzene ring have different substitutions and different degrees of oxidation, resulting in a range of phthalide compounds having various structures. Various dimers and trimers can also be formed.

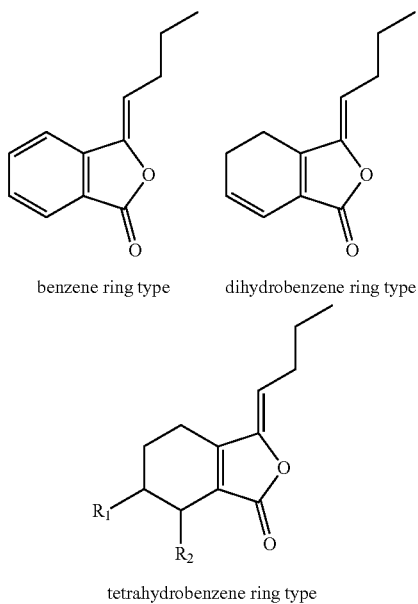

benzene ring type    dihydrobenzene ring type tetrahydrobenzene ring type

Ligustilide has many reaction sites, a relatively strong reactivity, and a relatively low relative free energy due to the highly unsaturated and conjugated system having three olefinic bonds and one carbonyl double bond but no stable conjugated system of aromatic ring formed. Thus, it is prone to 1,2, 1,4 and 1,6-Diels-Alder reactions to form complex dimer or trimer compounds.

Frank R. Stermita tried to obtain amide compounds through nucleophilic substitution reaction on the lactone ring using the aromatic amine; however, this amide finally leads to a cyclized reaction product through the intramolecular cycloaddition transition state (John J. Beck, Frank R. Stermitz, Addition of methyl thioglycolate and benzylamine to (Z)-ligustilide, a bioactive unsaturated lactone constituent of several herbal medicines. an improved synthesis of (Z)-ligustilide, Journal of Natural Products, 1995, 58(7): 1047-1055). Accordingly, each double bond or functional group of ligustilide has a relatively high reactivity. The chemical reaction conditions for the chemical reactions using ligustilide as raw material must be strictly controlled to achieve ideal chemical reaction designs.

For the chemical structure modifications on butylphthalide, Ji Hui et al. tried to introduce the nitroglycerin pharmacophore so as to improve the inhibitory activity of such compounds on platelet aggregation and increase the anti-inflammatory activity through NO inhibition, and the activity of the synthesized compound is significantly improved over butylphthalide (Wu Jing, Ling Jingjing, Wang Xuliang, Wang Xiaoli, Liu Jingchao, Ji Hui, Zhang Yihua, Synthesis and antiplatelet aggregation activity of isosorbide mononitrate-based butylphthalide derivatives, Chinese Journal of Medicinal Chemistry, 2012, 22(6): 483-489).

Domestic and foreign literatures show that the structural modifications on phthalide compounds can significantly improve the pharmacological activity of such compounds. However, for highly unsaturated ligustilide, the reaction conditions are relatively harsh and the reaction products are difficult to control. The reaction conditions and reaction catalyst systems must be carefully designed and controlled to achieve efficient and target syntheses. The pharmacological activity studies have shown that for the compounds based on ligustilide and having stable systems established through the Diels-Alder reaction, the pharmacological activity is relatively poor. Thus, the structural derivation of ligustilide should focus on the optimization of the substitution and addition of the lactone ring.

Butylphthalide is the first innovative drug with own independent intellectual property right in China. It was originally extracted and isolated from cress seed, and then chemically synthesized. Butylphthalide has a unique dual mechanism of action. It can reconstruct the microcirculation and increase ischemic deperfusion, thereby protecting the integrity of the blood vessel structure, restoring the diameter of the blood vessel, and increasing the blood flow in the ischemic area and the number of surrounding microvessels. It can also protect mitochondria and reduce cell death, thereby protecting the integrity of mitochondrial structure, increasing the activity of mitochondrial complex enzyme IV, increasing the activity of ATPase, and maintaining the stability of mitochondrial membrane. The cerebral stroke is resisted by double actions. Studies have shown that compared to neuroprotective effects of ligustilide and toxic side effects of the compound, butylphthalide is inferior to ligustilide in terms of pharmacological properties, due to its significant chemical structure characteristics.

Obviously, due to the chemical instability commonly known for phthalide compounds, although such compounds have better pharmacological activities, the developments and wide applications of such compounds in related products in the fields of medicine, health product, food and cosmetic are greatly limited. Therefore, to solve the problem for the developments and applications of products, the stability problem of such compounds must be addressed first. Due to the obvious chemical structural characteristics, ligustilide has a stronger pharmacological activity than butylphthalide. However, from a comprehensive comparison in terms of pharmaceutical effectiveness, safety, and quality controllability, butylphthalide has pharmaceutical properties (stable chemical structure), and thus has been approved by SFDA for marketing. Due to its activity and toxic side effects in clinical responses, which cannot meet the clinical requirements for the treatment of stroke, clinicians have put forward a strong demand for further optimizing butylphthalid and improving its activity. Therefore, it is necessary to artificially intervene in the unique chemical structure of ligustilide and optimize and screen out effective and stable drugs which are based on such compounds and useful for treating cardiovascular and cerebrovascular diseases.

SUMMARY OF THE INVENTION

An objective of the present invention is to provide a phthalide derivative as well as preparation method and use thereof. The remarkable characteristic of the phthalide derivative lies in that its original lactone structure fragment is replaced by a lactam group and the C-3 position is substituted by a hydroxyl group.

Therefore, the present invention provides a phthalide derivative of Formula I or Formula II, an optical isomer or pharmaceutically acceptable salt thereof, or their mixtures (e.g., a racemic mixture)

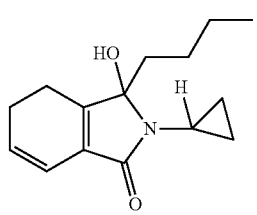

Formula I

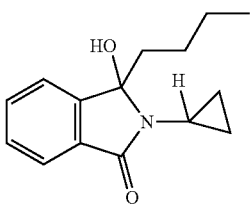

Formula II

In a preferred embodiment, the phthalide derivative is N-cyclopropyl-3-n-butyl-3-S-hydroxy-ligusticum lactam, N-cyclopropyl-3-n-butyl-3-R-hydroxy-ligusticum lactam, N-cyclopropyl-3-n-butyl-3-S-hydroxy-phthalide lactam or N-cyclopropyl-3-n-butyl-3-R-hydroxy-phthalide lactam.

In another aspect, the present invention provides a method for preparing a phthalide derivative (e.g., the phthalide derivative of Formula I or Formula II), comprising reacting the phthalide compound with cyclopropylamine in an organic solvent, wherein the original lactone structure fragment in the phthalide compound is replaced by a lactam group and the C3-position of the phthalide compound is substituted by a hydroxyl group, so as to obtain the phthalide derivative of Formula I or Formula II.

In a preferred embodiment, the method of the present invention has one, two, three, or four of the following features:
1) the phthalide compound is a benzene ring type, a dihydrobenzene ring type, or a tetrahydrobenzene ring type of phthalide compound with n-butenyl substitution at C3-position, preferably ligustilide or n-butenylphthalide, wherein the ligustilide or n-butenylphthalide is in the form of individually separate compound or in the form of a mixture of Angelica or Ligusticum plant extract, more preferably the plant extract is Angelica sinensis volatile oil extract or Ligusticum wallichii volatile oil extract or a mixture thereof;
2) the reaction is carried out at −20° C. to 60° C., and preferably carried out under stirring;
3) the organic solvent is a nonpolar organic solvent, preferably selected from cyclohexane, petroleum ether, tetrahydrofuran, and diethyl ether; and/or
4) the method also comprises a step of chiral resolution of enantiomers, preferably by chiral chromatography or chiral recrystallization.

In a preferred embodiment, in the preparation method, the molar ratio of the phthalide compound to cyclopropylamine is 1:1 to 1.2.

In a preferred embodiment, the preparation method also comprises a step of recycling the organic solvent under reduced pressure and recrystallizing to obtain the target product, and the solvent used for the recrystallization preferably is one or two of petroleum ether, ethyl acetate, acetone, and diethyl ether.

In a preferred embodiment, the preparation method comprises: adding and dissolving a phthalide compound in an organic solvent, with the temperature controlled at −20° C. to 60° C.; adding a reaction solution of cyclopropylamine dissolved in an organic solvent, with the temperature controlled at −20° C. to 60° C.; stirring and reacting for 1-24 hours; recycling the organic solvent under reduced pressure; and recrystallizing to obtain the target product.

The present invention also provides the phthalide derivative of Formula I or Formula II according to the present invention prepared by the above method, an optical isomer or pharmaceutically acceptable salt thereof, or their mixtures.

In another aspect, the present invention also provides use of the phthalide derivative of Formula I or Formula II according to the present invention, an optical isomer or pharmaceutically acceptable salt thereof, or their mixtures in the manufacture of a medicament, wherein the medicament is useful as an antioxidant and/or useful for treating or preventing the following diseases: cardiovascular and cerebrovascular diseases, depression, Alzheimer's disease, (neuro-)inflammatory diseases, pain, neuronal cell damage, ischemia-reperfusion injury, cerebral infarction, cognitive impairment, or brain damage.

In a preferred embodiment, the medicament comprises a mixture of the compound of Formula I and the compound of Formula II as active ingredient, wherein the mass percentage of the compound of Formula I in the mixture is 1-99%, preferably 90% or more.

DETAILED DESCRIPTION OF THE INVENTION

More specifically, the present invention provides a phthalide derivative, characterized in the following structure of the derivative:

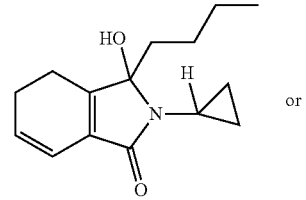

Formula I or

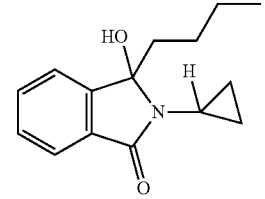

Formula II

As described above, the method for preparing a phthalide derivative comprises the following specific steps: adding and dissolving a phthalide compound in an organic solvent, with the temperature controlled at −20° C. to 60° C.; adding a reaction solution of cyclopropylamine dissolved in an organic solvent, with the temperature controlled at −20° C. to 60° C.; stirring and reacting for 1-24 hours; recycling the organic solvent under reduced pressure; and recrystallizing to obtain the target product.

The molar ratio of the phthalide compound to the cyclopropylamine is from 1:1 to 1.2.

The phthalide compound is one or two or more of ligustilide, n-butenylphthalide, and a volatile oil extract comprising ligustilide or n-butenylphthalide from medicinal materials.

The volatile oil extract from medicinal materials is *Angelica sinensis* volatile oil extract or *Ligusticum wallichii* volatile oil extract.

The organic solvent is a nonpolar organic solvent, preferably cyclohexane, petroleum ether, tetrahydrofuran, and the like.

The solvent used for the recrystallization is one or two of petroleum ether, ethyl acetate, acetone, and diethyl ether.

Use of the phthalide derivative as described above for prevention or treatment of cardiovascular and cerebrovascular diseases and use in anti-oxidation are also disclosed.

The phthalide derivative is a composition of the compound of Formula I and the compound of Formula II, wherein the mass percentage of the compound of Formula I in the composition is 1-100%.

The mass percentage of the compound of Formula I is 90% or more (e.g., 91%, 92%, 93%, 94%, 95%, 96%, 97%, 98%, and 99%).

The chemical structure of each of the phthalide derivatives synthesized by the chemical structure derivatization method in the present invention is proved to conform to the target compounds by various detection techniques such as mass spectrometry (HR-ESI-MS), nuclear magnetic resonance (1D, 2D-NMR), single crystal diffraction (X-Ray), and liquid chromatography (HPLC-DAD).

The phthalide derivatives in the present invention are demonstrated to have good anti-oxidantive nerve cell protection and anti-platelet aggregation effects through in vivo and in vitro pharmacological activity studies, and can be used as chemo-preventive and therapeutic drugs for cardiovascular and cerebrovascular diseases.

The advantages of the present invention include the following:

1. The subject matter compound of the present invention belongs to an isoindolinone compound. Under the achiral synthesis reaction conditions, enantiomers with racemization at C-3 position are generated from the compound of Formula I through self-cyclization nucleophilic substitution within the molecule. Then, the chiral compounds as individual enantiomers having C-3 hydroxyl group in the S- and R-configurations are obtained by simple resolution methods such as recrystallization.

2. The phthalide derivatives are constructed and prepared by the chemical structure derivatization based on the unique chemical structure and significant pharmacophore of cyclopropylamine. Commonly known unstable oily substances of phthalide compounds are converted into colorless crystalline solids. The chemical structure stability of the compounds is enhanced, the stability of natural or organic synthetic phthalide compounds is effectively enhanced, the drugability of the compounds is increased, and the bad volatile odor of the compounds is effectively masked. For example, ligustilide is the main component of volatile oil. It is an oily substance, unstable, and has poor drugability. Its instability is well-known in the art. It becomes a crystalline solid after our structural derivatization, indicating that the stability is greatly enhanced.

3. The phthalide derivatives prepared through chemical structure derivatization form a unique stereochemical structure, which enhancing the spatial binding degrees of such compounds to the drug target, and effectively enhancing the pharmacological activities of such compounds. Without being limited to a particular theory, it is believed that in the reactions of such compounds, cyclopropylamine first undergoes a nucleophilic substitution reaction with the carbonyl group in the ligustilide ring, to form a key ring-opening intermediate of amide and 1-pentanone, wherein the nitrogen atom in cyclopropane in this intermediate has a relatively strong nucleophilic reaction activity, and continues to undergo a nucleophilic addition reaction with the ketocarbonyl group in the 1-pentanonyl. However, at this time, the cyclopropyl group in the cyclopropylamine can be regarded as a highly conjugated planar structure. Due to the effect of steric hindrance, the free rotation of the carbon-nitrogen bond formed by the carbon in the carbonyl group and the nitrogen in the cyclopropylamine is suppressed, and to reduce the steric hindrance, the occurrence of the nucleophilic addition reaction on the 1-pentanonyl is facilitated. As a result, the cyclopropane and hydroxyl group have relatively small steric structures and space volumes, and both are biased to the same side of the planar structure formed by lactam and hexadiene, while the 4-carbon aliphatic alkane side chain with a larger space volume tends to lie in another side. Thus, such phthalide compounds react with cyclopropylamine to form unique stereochemical structure reaction products.

4. The phthalide compounds obtained through structure modifications in the present invention enrich the chemical structure library for such compounds, and provide a large number of lead compounds for the drug screening from such compounds.

BRIEF DESCRIPTION OF THE DRAWINGS

FIG. 9 shows the single crystal diffraction (X-Ray) structure of the compound N-cyclopropyl-3-n-butyl-3-S-hydroxy-ligusticum lactam, wherein FIG. 9a shows the single crystal structure, and FIG. 9b shows the bimolecular single crystal structure within the lattice cell, wherein a single enantiomer having an S configuration as the spatial configuration at C-3 position is shown.

Figure 11:
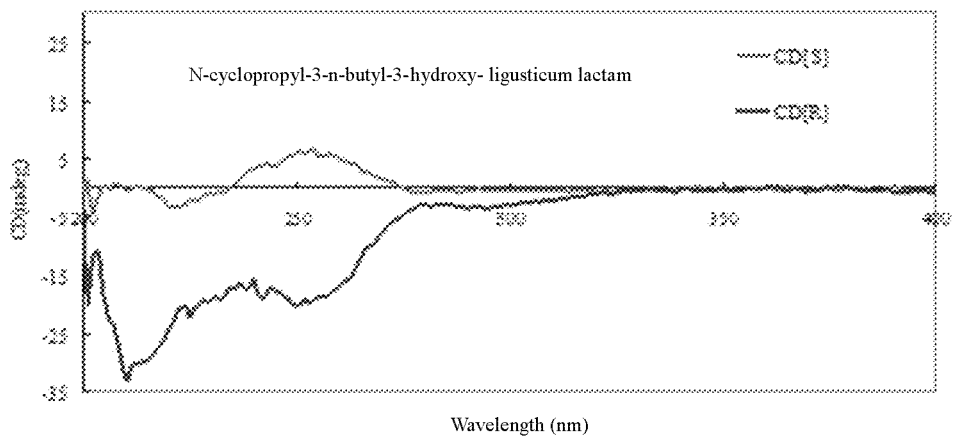

FIG. 11 shows the circular dichroism (CD) spectra of R- and S-enantiomers of N-cyclopropyl-3-n-butyl-3-S-hydroxy-ligusticum lactam.

Figure 12:
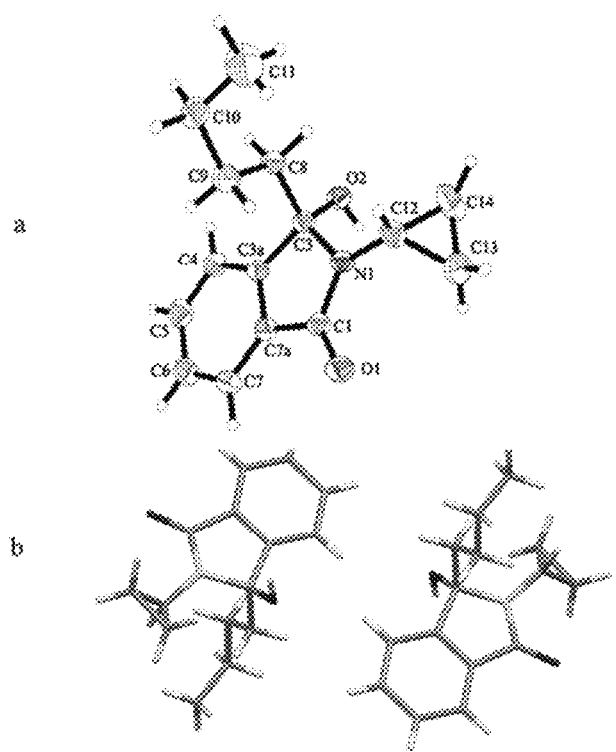

FIG. 12 shows the single crystal X-Ray derived structure of the compound N-cyclopropyl-3-n-butyl-3-hydroxy-phthalide lactam; wherein FIG. 12a shows the single crystal structure, and FIG. 12b shows the bimolecular single crystal structure within the lattice cell, and the figure shows a racemate in which both R- and S-configurations exist as the spatial configuration at C-3 position.

Figure 13:
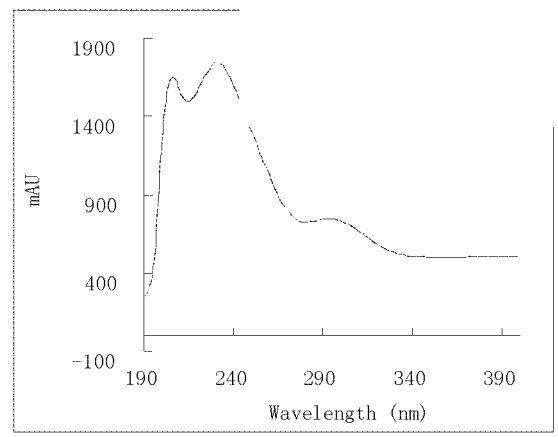

FIG. 13 shows the UV spectrum of the compound N-cyclopropyl-3-n-butyl-3-hydroxy-phthalide lactam by DAD detection.

Figure 10:
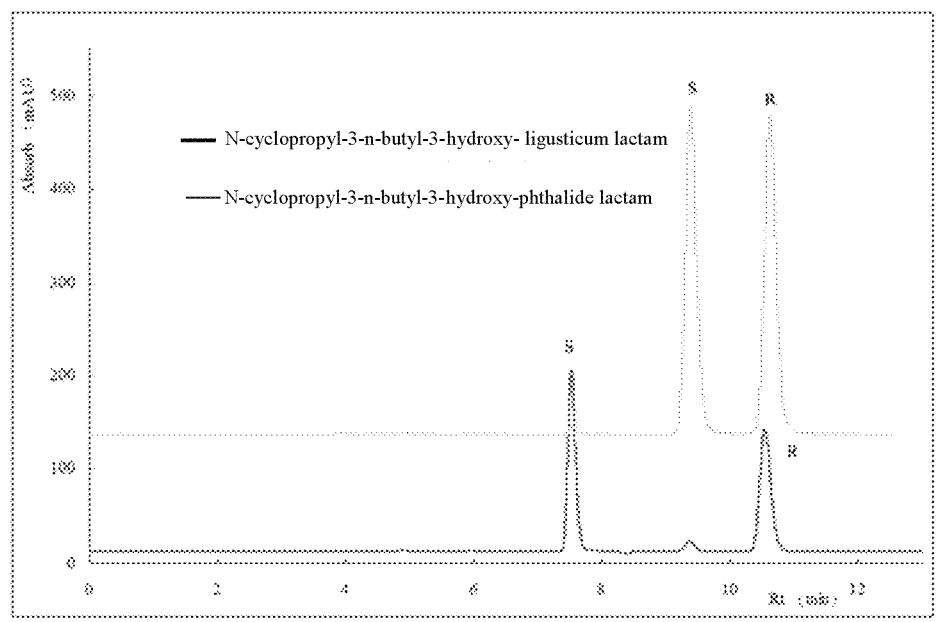
FIG. 10 shows the HPLC-DAD chiral resolution chromatograms of the compound N-cyclopropyl-3-n-butyl-3-hydroxy-phthalide lactam and the compound N-cyclopropyl-3-n-butyl-3-hydroxy-ligusticum lactam. Detection instrument: Agilent 1200 Chromatography System equipped with DAD detector; Chromatography conditions: chromatography column: FMG-ACS-A01-NFC Chiral ND(2)(250 mm×4.5 mm, 5 μm); Mobile phase: n-hexane:ethanol (V:V) =90:10 (v/v); injected by manual injector, 20 μL per injection; Detection wavelength: 283 nm, wherein S and R denote corresponding enantiomers, respectively.
Figure 14:
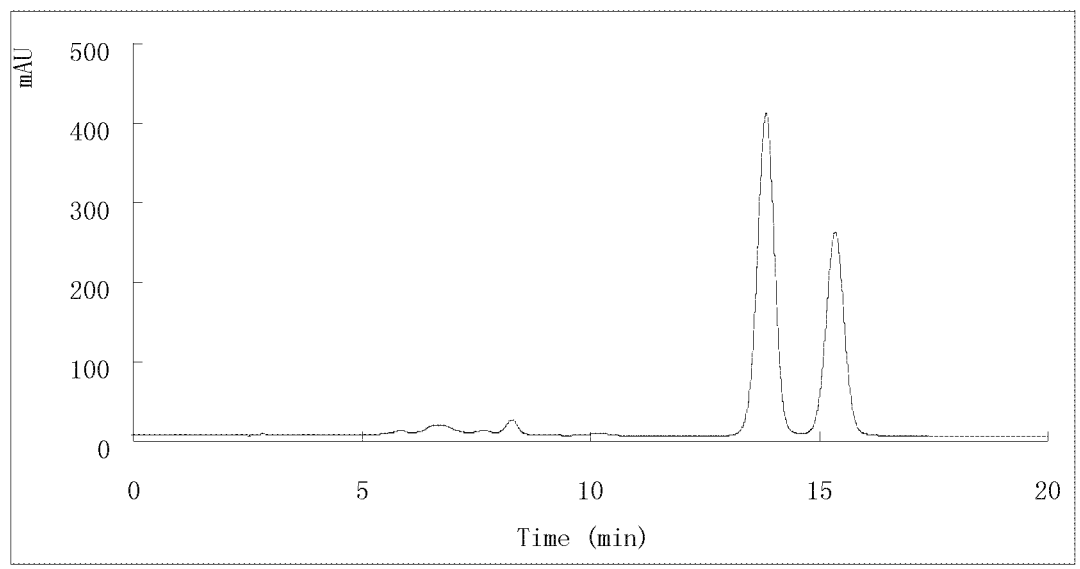

FIG. 14 shows the detection result for a mixed sample of the compound N-cyclopropyl-3-n-butyl-3-S-hydroxy-ligusticum lactam and the compound N-cyclopropyl-3-n-butyl-3-hydroxy-phthalide lactam by HPLC-DAD chromatography, in which the chromatographic peak at TR=13.840 min is that of N-cyclopropyl-3-n-butyl-3-hydroxy-phthalide lactam, and the chromatographic peak at TR=15.348 min is that of N-cyclopropyl-3-n-butyl-3-S-hydroxy-ligusticum lactam. The chromatography conditions are the same as those in FIG. 10.

Figure 15:
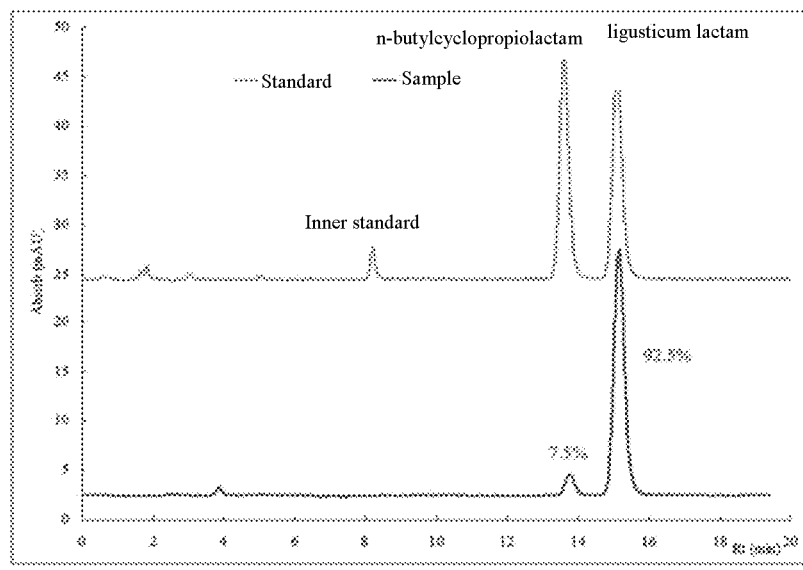

FIG. 15 shows the HPLC-DAD method for determining the contents of the target compounds N-cyclopropyl-3-n-butyl-3-hydroxy-ligusticum lactam and N-cyclopropyl-3-n-butyl-3-hydroxy-phthalide lactam by area normalization.

Figure 16:
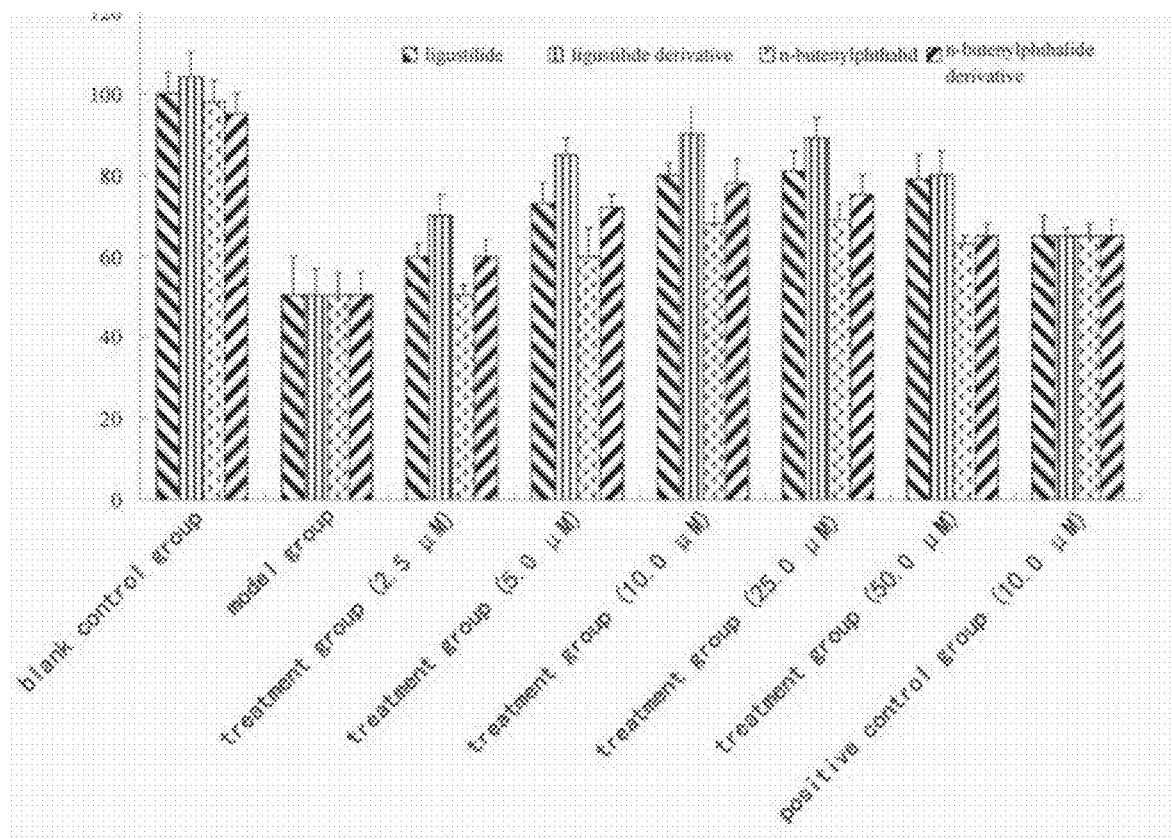

FIG. 16 shows the protection effect of the phthalide derivative on hydrogen peroxide-induced oxidative damage to PC12 nerve cells, wherein "**" represents a statistically significant difference with $p<0.01\%$; and "*" represents a statistically significant difference with $p<0.05\%$.

Figure 17:
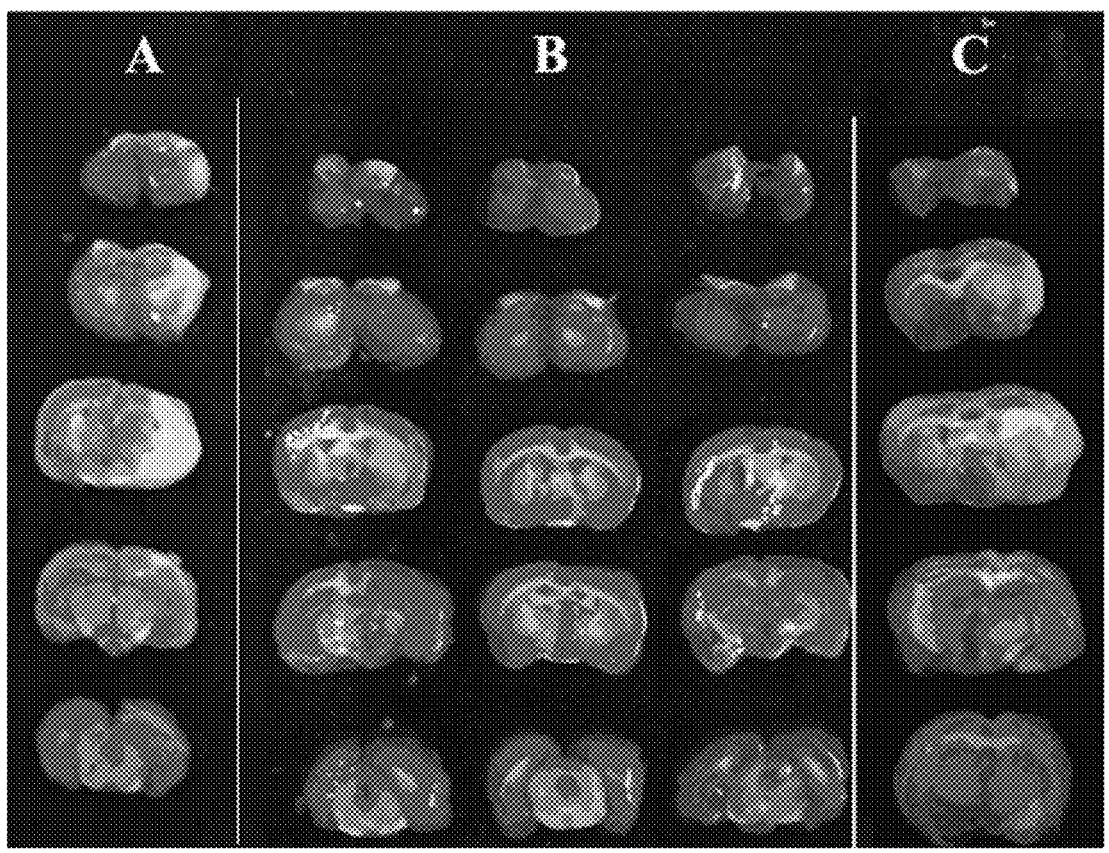

FIG. 17 shows the therapeutic effect of the phthalide derivative on the acute cerebral ischemic infarction in the unilateral suture-occluded model of Wistar rat. A. model control, infarct area: 30.57%; B. complete recanalization in the ligustilide derivative treatment group (dosing for 3 days after modeling, 40 mg/kg, intraperitoneal injection); C. ligustilide derivative prevention therapy group (pre-dosing for 3 days, modeling, dosing for another 3 days; 40 mg/kg, intraperitoneal injection), infarct area: 22%.

Figure 18:
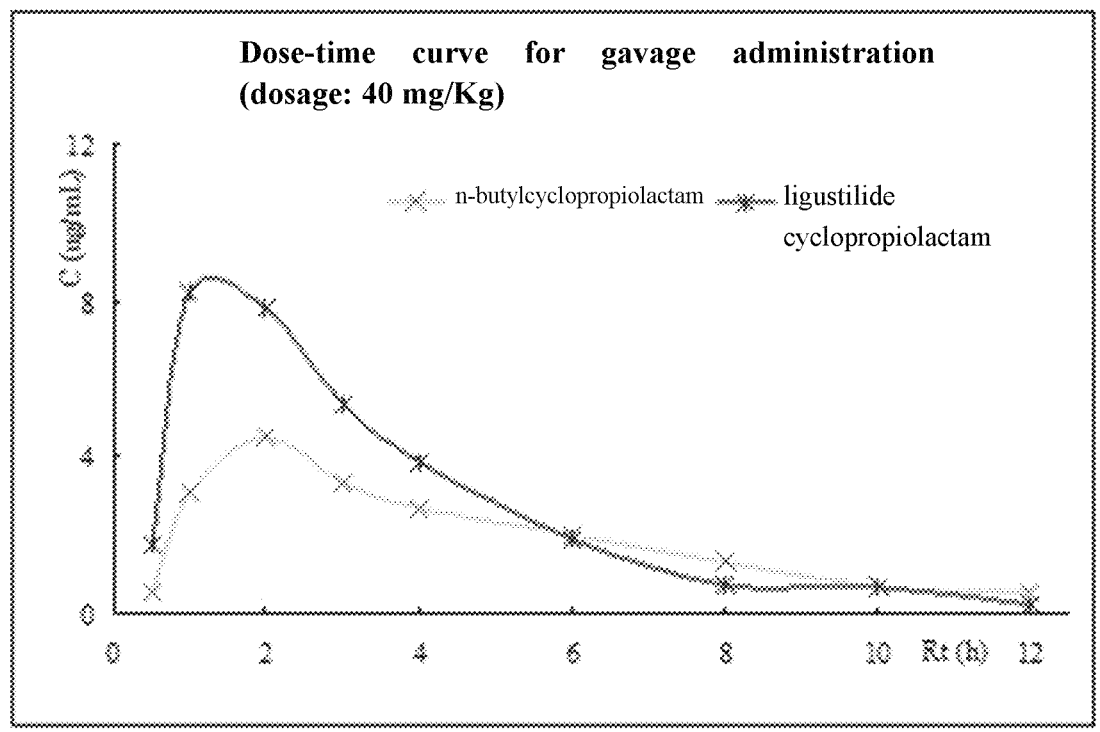

FIG. 18 is a graph showing the dose-time curve of the phthalide derivative administrated to the rat by gavage.

Figure 19:
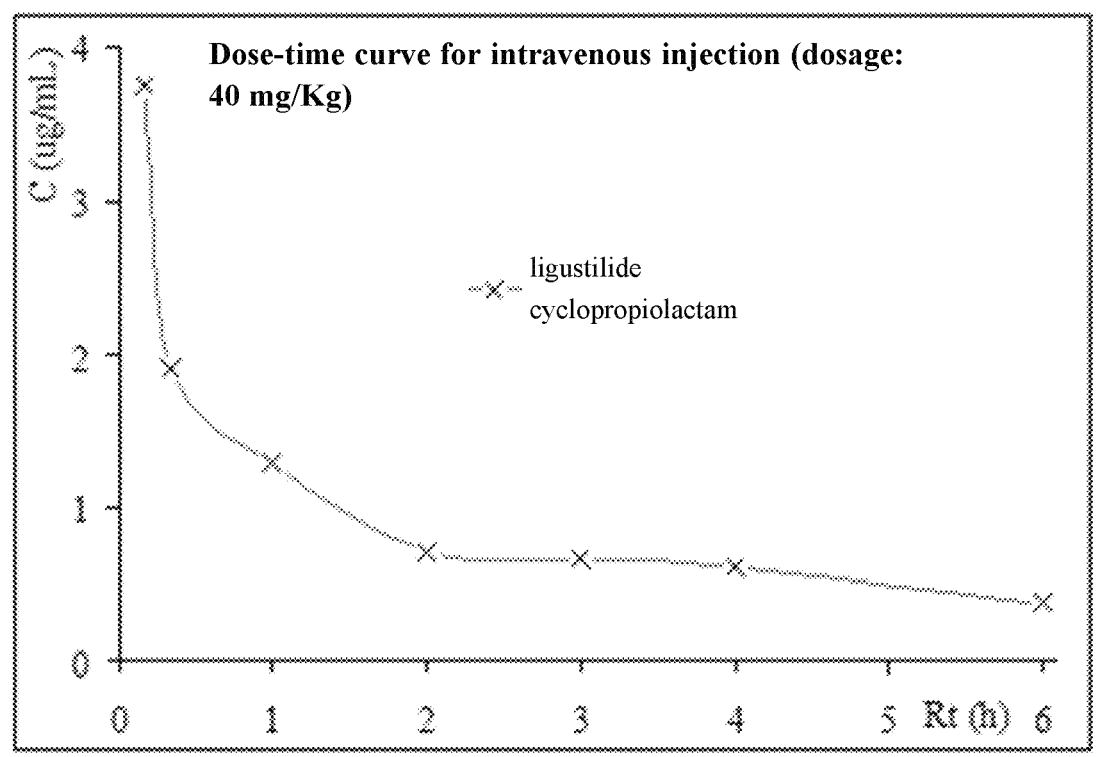

FIG. 19 is a graph showing the dose-time curve of the phthalide derivative administrated to the rat by intravenous injection.

DESCRIPTION OF EMBODIMENTS

Example 1

1) Synthesis of N-cyclopropyl-3-n-butyl-3-hydroxy-ligusticum Lactam

Figure 1:
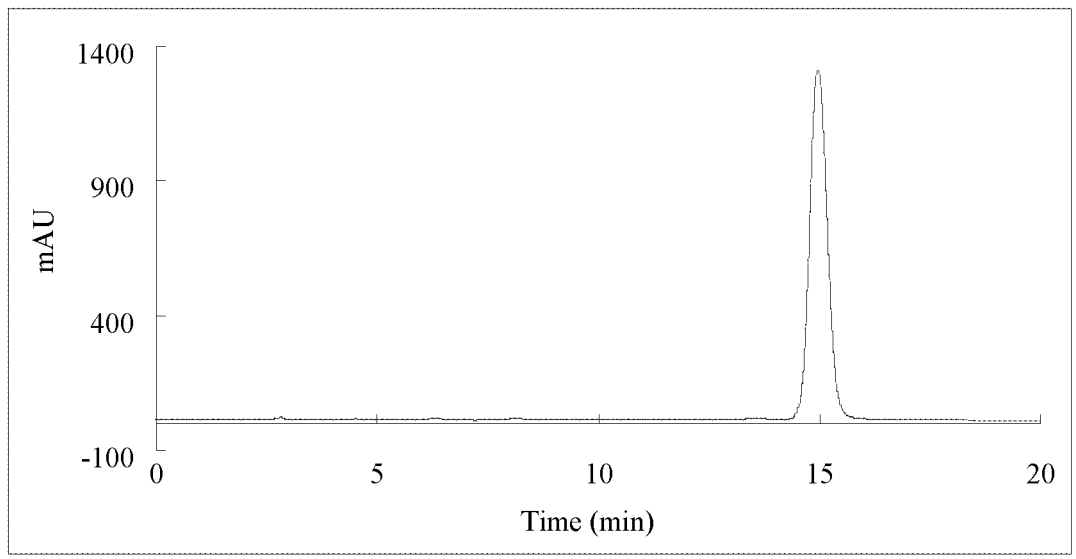
FIG. 1 shows the HPLC-DAD chromatography detection result of the compound N-cyclopropyl-3-n-butyl-3-S-hydroxy-ligusticum lactam, in which the chromatographic peak at TR=14.863 min represents the target compound. Detection instrument: Agilent 1200 Chromatography System equipped with DAD detector; Chromatography conditions: chromatography column: XTerra MS $C_{18}$ (Waters); filler particle size: 5 μm, column length: 4.6×250 mm; Mobile phase: methanol:water=65:35 (V/V); injected by manual injector, 20 μL per injection; Detection wavelength: 280 nm.
Figure 2:
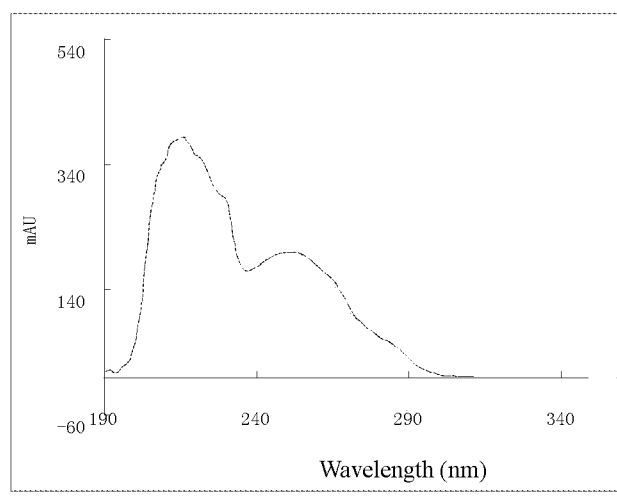
FIG. 2 shows the UV spectrum of the compound N-cyclopropyl-3-n-butyl-3-S-hydroxy-ligusticum lactam by DAD detection.
Figure 3:
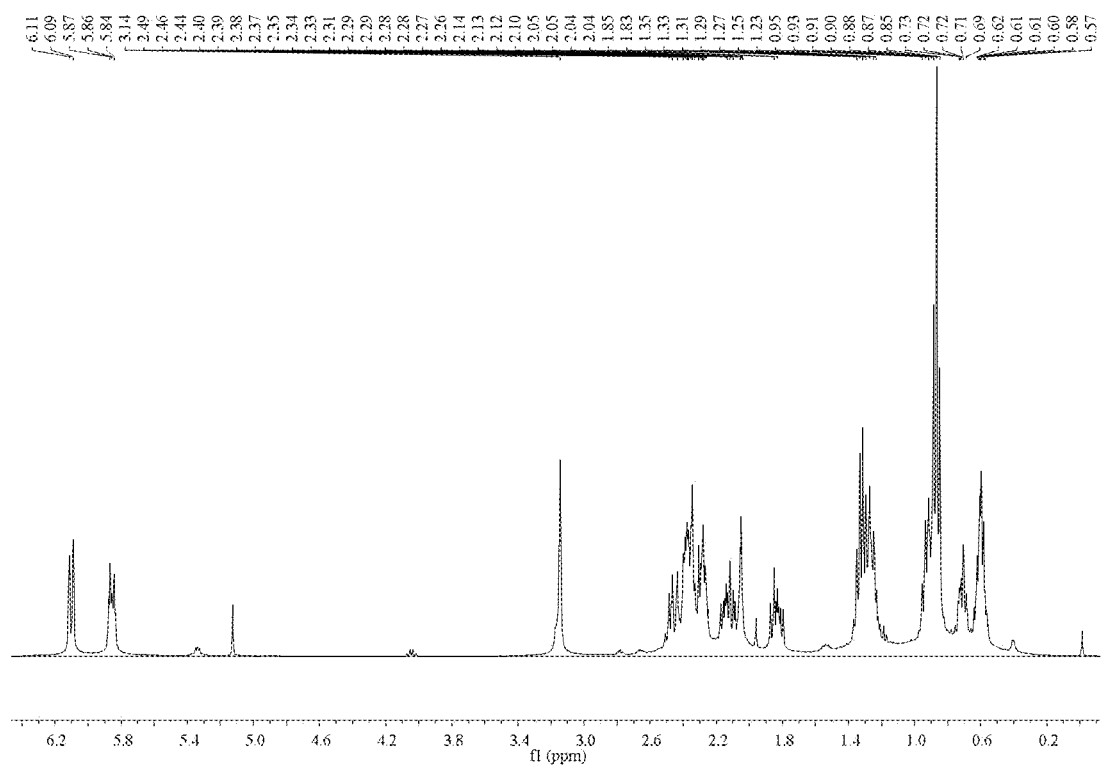
FIG. 3 shows the $^1$H-NMR spectrum of the compound N-cyclopropyl-3-n-butyl-3-S-hydroxy-ligusticum lactam.
Figure 4:
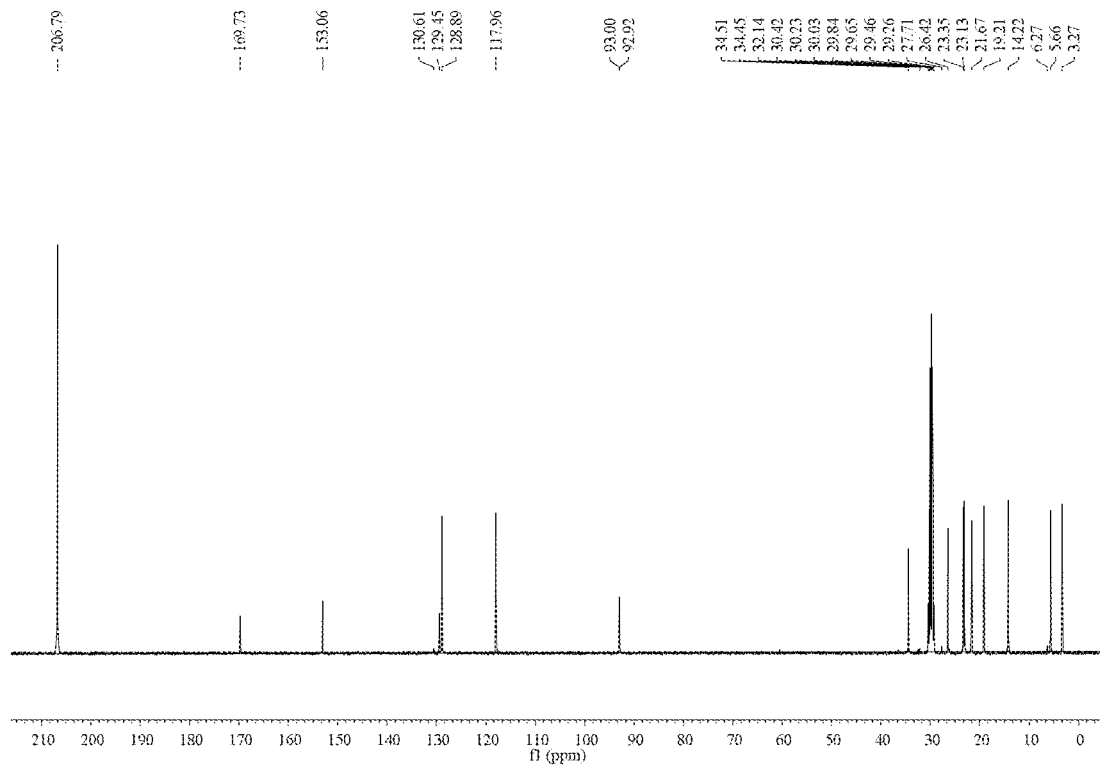
FIG. 4 shows the $^{13}$C-NMR spectrum of the compound N-cyclopropyl-3-n-butyl-3-S-hydroxy-ligusticum lactam.
Figure 5:
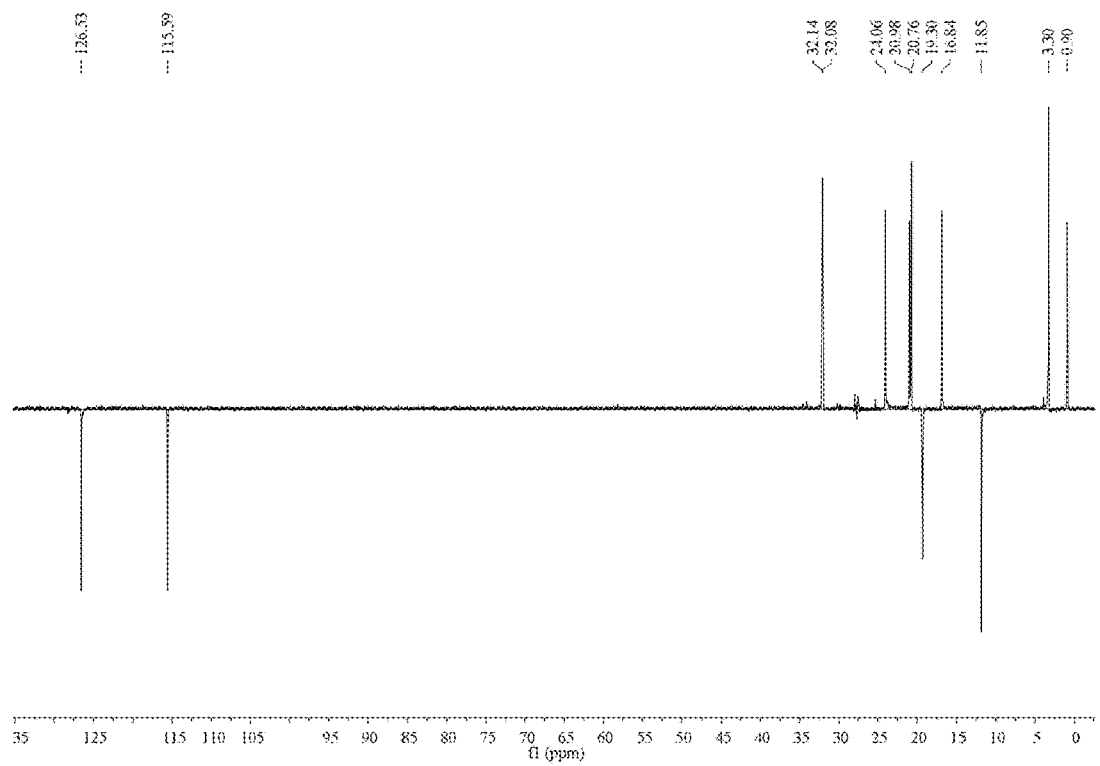
FIG. 5 shows the DEPT spectrum of the compound N-cyclopropyl-3-n-butyl-3-S-hydroxy-ligusticum lactam.
Figure 6:
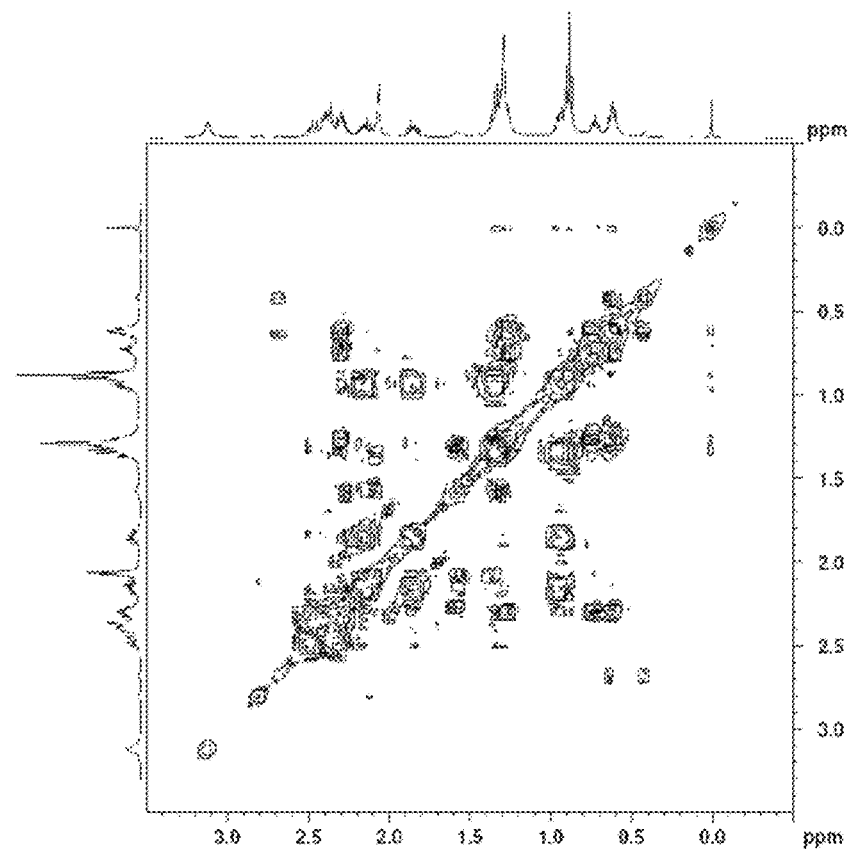
FIG. 6 shows the $^1$H-$_1$HCOSY spectrum of the compound N-cyclopropyl-3-n-butyl-3-S-hydroxy-ligusticum lactam.
Figure 7:
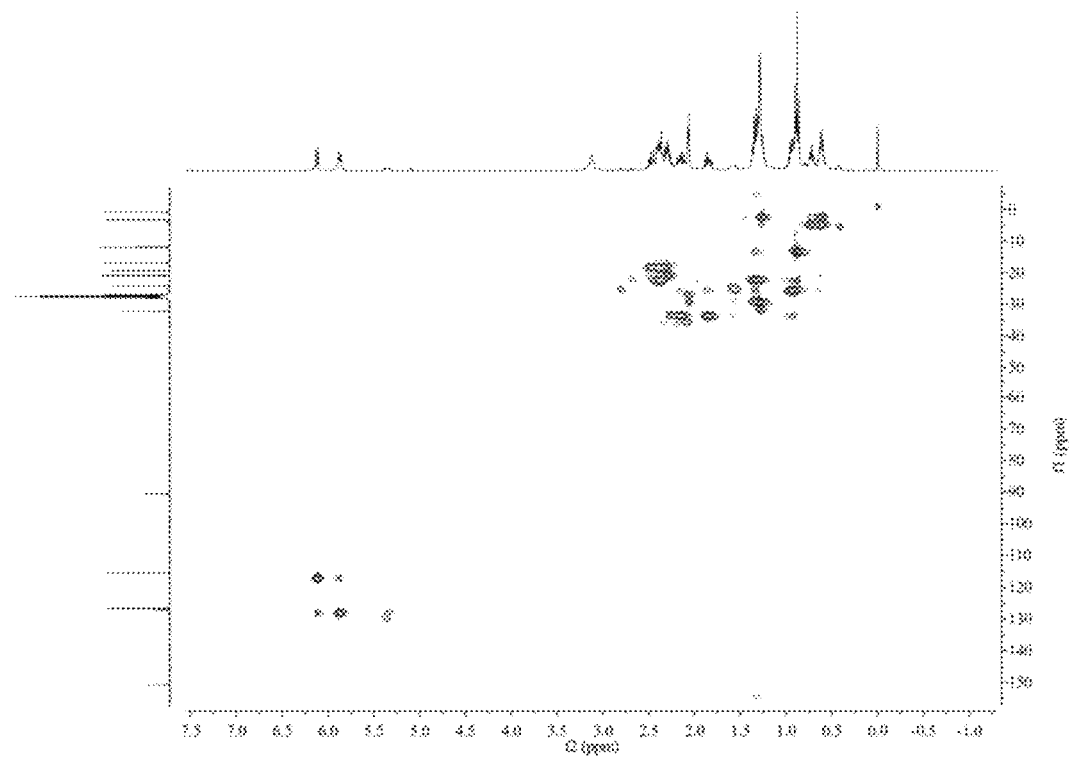
FIG. 7 shows the HSQC spectrum of the compound N-cyclopropyl-3-n-butyl-3-S-hydroxy-ligusticum lactam.
Figure 8:
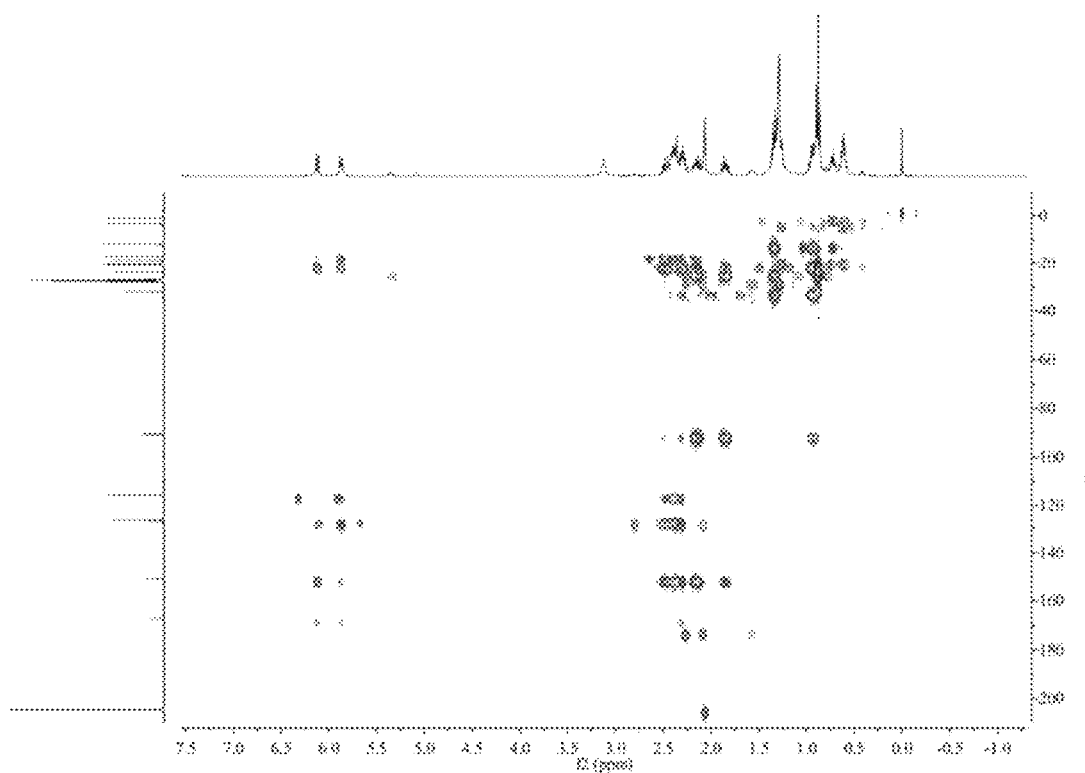
FIG. 8 shows the HMBC spectrum of the compound N-cyclopropyl-3-n-butyl-3-S-hydroxy-ligusticum lactam.
Figure 9:
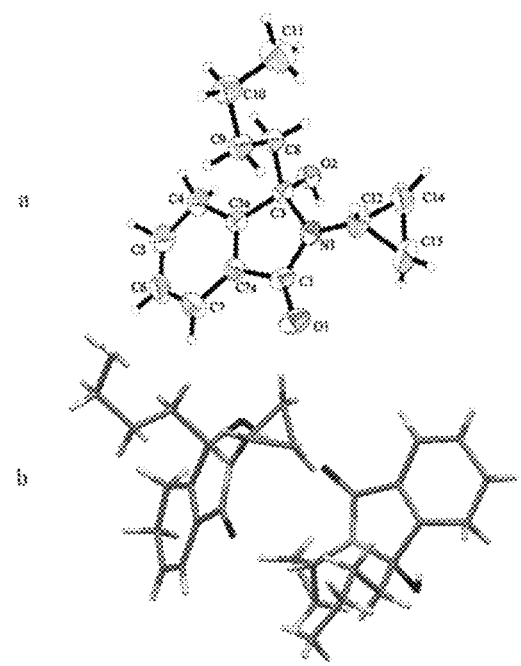

Ligustilide (extracted from *Angelica sinensis*, separated and purified in the present inventor's laboratory (for the extraction method, see Liu Lusi, Yue Meiying, Li Wenbing, Peng Cheng, Xiong Liang. Difference study on chemical components and their protective effect on acute cerebral injury between the oils from *Angelica sinensis* and *Ligusticum* chuanxiong, Pharmacology and Clinics of Chinese Materia Medica, 2016, 32(6): 105-108), the detected content is 98% by area normalization in the HPLC method) (1.900 g, 0.010 mol) was dissolved in 50 mL of tetrahydrofuran, and cyclopropylamine (0.684 g, 0.012 mol) was dissolved in 20 mL of tetrahydrofuran. The temperature of water bath was controlled at 25° C. Under mechanical stirring, the solution of cyclopropylamine in tetrahydrofuran was dropwise added to the solution of ligustilide in tetrahydrofuran, and the reaction was carried out under stirring for 4 h. The tetrahydrofuran and excess cyclopropylamine solution were recycled by rotary evaporation under reduced pressure. 200 mL of petroleum ether was added to the above concentrate, mixed uniformly, and left to stand overnight until the synthesized product crystals were precipitated, then filtered by suction, to obtain 1.976 g of crude product (product yield: 80%). The crude product was recrystallized from a mixed solvent of petroleum ether and acetone (5:1, V/V), to obtain 0.97 g of crystal product (crystal yield: 49%). Using a HPLC-DAD method, the content of the target compound determined by area normalization reached 99.5% (see FIGS. 1 and 2). For the target compound, it was confirmed as the target compound by MS, NMR, and X-Ray single crystal diffraction techniques (see FIGS. 3-9).

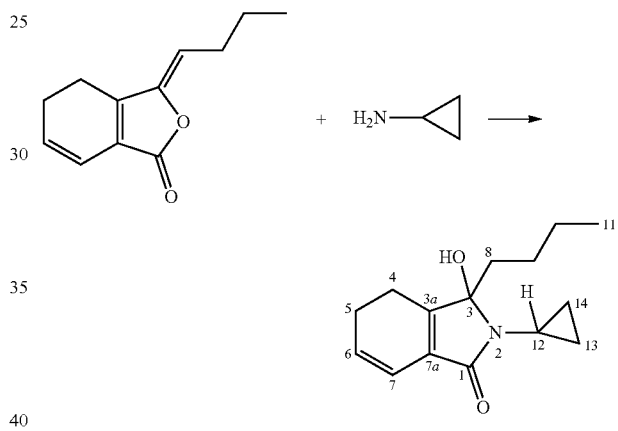

N-cyclopropyl-3-n-butyl-3-hydroxy-ligusticum lactam: colorless acicular or prismatic crystal, melting point: 116° C.-118° C., HR-ESI-MS m/z 270.1465 [M+H]$^+$ (calculated for $C_{15}H_{21}NNaO_2$: 270.1470), $^1$H-NMR (400 MHz, Acetone-d$_6$): δ 6.11 (1H, dt, J=12.0, 4.0 Hz, H-7), 5.86 (1H, dt, J=8.0, 4.0, Hz, H-6), 2.49-2.43 (1H, m, H-4), 2.41-2.34 (1H, m, H-4), 2.39-2.36 (2H, m, H-5), 2.31-2.27 (1H, m, H-12), 2.17-2.11 (1H, m, H-8), 1.88-1.82 (1H, m, H-8), 1.35-1.31 (2H, m. H-10), 1.28-1.22 (1H, m, 1.27-1.25 (1H, m, H-13), 0.96-0.90 (2H, m. H-9), 0.88-0.85 (3H, t, J=8.0 Hz, H-11), 0.75-0.69 (1H, m, H-14), 0.64-0.58 (1H, m, H-13), 0.63-0.58 (1H, m, H-14); $^{13}$C-NMR (100 MHz, Acetone-d$_6$): δ 169.2 (C-1), 152.6 (C-3a), 128.9 (C-7a), 128.3 (C-6), 117.4 (C-7), 92.4 (C-3), 33.9 (C-8), 25.9 (C-9), 22.6 (C-10), 21.1 (C-12), 13.7 (C-11), 5.1 (C-14), 2.7 (C-13).

Lattice parameters: orthorhombic crystal system, space group P2$_1$2$_1$2$_1$, a=7.8762 (15), b=10.576 (2), c=16.809 (3), α=β=γ=900, lattice volume: V=1400.1 (5), the number of molecules within the lattice cell: Z=4, the instrument used: Bruker APEX II plane detector, the irradiation wavelength used: 0.71073, the radiation source: MoKa, the collected independent diffraction points: 2876, in which the effective diffraction points: 2037; the diffraction points for refinement: 2876; the number of participating parameters: 165; R$_1$ value for all diffraction points: 0.0775; R$_1$ value for detectable diffraction points: 0.0531; wR$_2$ value for all diffraction points: 0.1348; wR$_2$ value for detectable diffraction points: 0.1203; S value for detectable diffraction points: 1.003; S value for all diffraction points: 1.003; maximum shift value during final refinement process: 0.000.

2) Chiral resolution and configuration determination of N-cyclopropyl-3-n-butyl-3-hydroxy-ligusticum lactam enantiomer 500 mg of the compound synthesized in 1) as above was dissolved in 2 mL of a mixed solvent of n-hexane and ethanol (V:V, 90:10). The compounds were prepared through chiral resolution by continuous liquid chromatography, using the cellulose chiral coating type bonded stationary phase derived from trisubstituted 3,5-dimethylphenyl isocyanate as chromatography column and using normal phase chromatography system (n-hexane:ethanol, V:V, 90:10) as mobile phase. The fractions of 7.623 min and 10.544 min were collected (see FIG. 10). The solvents were recycled under reduced pressure. The single crystals were cultured using a petroleum ether/acetone solvent system, and the absolute spatial configuration was determined by X-Ray diffraction. A target compound solution at a concentration of 0.1 mg/mL was prepared, and subjected to the measurement by circular dichroism spectrum (CD) (see FIG. 11) and optical rotation measurement, to assist in the determination of the absolute configuration of the compound.

The chromatography conditions were as follows: FMG-ACS-A01-NFC Chiral ND(2)(250 mm×4.5 mm, 5 μm), mobile phase: n-hexane:ethanol (V:V)=90:10, detection wavelength: 254 nm. Tr=7.623 min refers to S-(+)-ligustilide cyclopropiolactam, accounting for 49.2%; and Tr=10.544 min refers to R-(−)-ligustilide cyclopropiolactam, accounting for 50.8%. By the area normalization ratio between R- and S-compounds in the chiral chromatography, it can be determined that the chiral products generated by the synthesis reaction of ligustilide and cyclopropane are enantiomers in an equivalent amount.

In circular dichroism spectra, N-cyclopropyl-3-n-butyl-3-hydroxy-ligusticum lactam in the S configuration has a significant positive cotton effect at 254 nm, while N-cyclopropyl-3-n-butyl-3-hydroxy-ligusticum lactam in the R configuration has a significant negative cotton effect at 254 nm. The two compounds have completely opposite CD spectrum absorption characteristics. The determined optical data for N-cyclopropyl-3-n-butyl-3-hydroxy-ligusticum lactam in R- and S-configurations are as follows: (S)—N-cyclopropyl-3-n-butyl-3-hydroxy-ligusticum lactam (N-cyclopropyl-3-n-butyl-3-S-hydroxy-ligusticum lactam): optical value $[\alpha]_D^{27}=+138$ (C 0.5, CH$_3$OH), (R)—N-cyclopropyl-3-n-butyl-3-hydroxy-ligusticum lactam (N-cyclopropyl-3-n-butyl-3-R-hydroxy-ligusticum lactam) optical value $[\alpha]_D^{27}=-130$ (C 0.5, CH$_3$OH).

Example 2: Synthesis of N-cyclopropyl-3-n-butyl-3-hydroxy-phthalide Lactam n-butenylphthalide (1.880 g, 0.010 mol) (a product from Alfa Aesar, purity: 95%) was dissolved in 50 mL of tetrahydrofuran, and cyclopropylamine (0.684 g, 0.012 mol) was dissolved in 20 mL of tetrahydrofuran. Under mechanical stirring at room temperature, the solution of cyclopropylamine in tetrahydrofuran was dropwise added to the solution of ligustilide in tetrahydrofuran, and the reaction was carried out under stirring for 6 h. The tetrahydrofuran and excess cyclopropylamine solution were recycled by rotary evaporation under reduced pressure. 200 mL of petroleum ether was added to the above concentrate, mixed uniformly, and left to stand overnight until the synthesized product crystals were precipitated, then filtered by suction, to obtain 2.083 g of crude product (product yield: 85%). The crude product was recrystallized from a mixed solvent of petroleum ether and acetone (10:1, V/V), to obtain 1.666 g of crystal product (crystal yield: 80%). Using HPLC-DAD method, the content of the target compound determined by area normalization reached 99.6%. For the target compound, it was confirmed as the target compound by MS, NMR, and X-Ray single crystal diffraction techniques (see FIGS. 12 and 13). According to the chiral resolution method in Example 1, by the chiral resolution using high performance liquid chromatography, the compound was determined as a pair of chiral enantiomers (see FIG. 10).

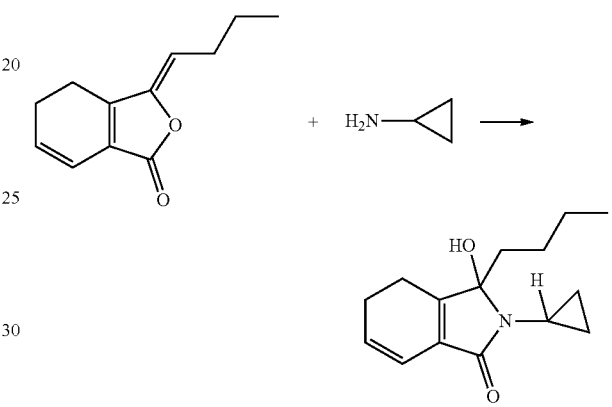

N-cyclopropyl-3-n-butyl-3-hydroxy-phthalide lactam: colorless acicular or prismatic crystal, HR-ESI-MS m/z 246.1492 [M+H]$^+$ (calculated for C$_{15}$H$_{20}$NO$_2$: 246.1489), $^1$H-NMR (400 MHz, Acetone-d$_6$): δ 7.63 (1H, d, J=8.0 Hz, H-7), 7.60 (1H, t, J=8.0, 4.0 Hz, H-5), 7.55 (1H, d, J=8.0 Hz, H-4), 7.49 (1H, t, J=8.0, 4.0 Hz, H-4), 2.45-2.50 (1H, td, J=8.0, 4.0 Hz, H-8), 2.38-2.38 (1H, td, J=12.0, 4.0 Hz, H-8), 2.25-2.16 (1H, td, J=16.0, 4.0 Hz, H-9), 2.05-2.07 (1H, m, H-12), 1.49-1.42 (1H, m, H-9), 1.30-1.18 (2H, m, H-10), 0.89-1.00 (1H, m, H-13), 0.82-0.87 (1H, m, H-13), 0.79 (3H, t, J=16.0, 8.0 Hz H-11), 0.58-0.76 (2H, m, H-14); $^3$C-NMR (100 MHz, Acetone-d$_6$): δ 166.2, 145.8, 130.4, 130.0, 127.3, 120.6, 120.2, 90.2, 34.4, 24.0, 20.5, 19.7, 11.6, 3.20, 0.90.

Example 3: Synthesis of a Mixture of the Compound N-cyclopropyl-3-n-butyl-3-hydroxy-ligusticum Lactam and the Compound N-cyclopropyl-3-n-butyl-3-hydroxy-phthalide Lactam Using Angelica sinensis Volatile Oil The prepared Angelica sinensis volatile oil was pre-separated by column chromatography using petroleum ether and ethyl acetate (3:1, V/V) as eluent. The portion of Angelica sinensis volatile oil having a higher content of ligustilide (3.000 g) was dissolved in 60 mL of tetrahydrofuran, and cyclopropylamine (0.684 g, 0.012 mol) was dissolved in 30 mL of tetrahydrofuran. Under mechanical stirring, the solution of cyclopropylamine in tetrahydrofuran was dropwise added to the above solution of Angelica sinensis volatile oil in tetrahydrofuran, and the reaction was carried out under stirring for 10 h. The tetrahydrofuran and excess cyclopropylamine solution were recycled by rotary evaporation under reduced pressure. 200 mL of petroleum ether was added to the above concentrate, mixed uniformly, and left to stand overnight until the synthesized product crystals were precipitated, then filtered by suction, to obtain 2.283 g of crude product (product yield: 76%). The crude product was recrystallized from a mixed solvent of petroleum ether and acetone (10:1, V/V), to obtain 1.872 g of crystal product (crystal yield: 82%). Using HPLC-DAD method, the contents of the target compounds were determined by area normalization: the content of the compound N-cyclopropyl-3-n-butyl-3-hydroxy-ligusticum lactam is 90.0%; and the content of the compound N-cyclopropyl-3-n-butyl-3-hydroxy-phthalide lactam is 8.9% (see FIG. 14).

Example 4: Synthesis of a Mixture of the Compound N-cyclopropyl-3-n-butyl-3-hydroxy-ligusticum Lactam and the Compound N-cyclopropyl-3-n-butyl-3-hydroxy-phthalide Lactam Using *Ligusticum wallichii* Volatile Oil The obtained *Ligusticum wallichii* volatile oil was pre-separated by column chromatography using petroleum ether and ethyl acetate (3:1, V/V) as eluent. The portion of *Ligusticum wallichii* volatile oil having a higher content of ligustilide (3.500 g) was dissolved in 60 mL of tetrahydrofuran, and cyclopropylamine (0.684 g, 0.012 mol) was dissolved in 30 mL of tetrahydrofuran. Under mechanical stirring, the solution of cyclopropylamine in tetrahydrofuran was dropwise added to the above solution of *Ligusticum wallichii* volatile oil in tetrahydrofuran, and the reaction was carried out under stirring for 10 h. The tetrahydrofuran and excess cyclopropylamine solution were recycled by rotary evaporation under reduced pressure. 200 mL of petroleum ether was added to the above concentrate, mixed uniformly, left to stand overnight until the synthesized product crystals were precipitated, then filtered by suction, to obtain 1.982 g of crude product (product yield: 56.7%). The crude product was recrystallized from a mixed solvent of petroleum ether and acetone (10:1, V/V), to obtain 1.685 g of crystal product (crystal yield: 85%). Using HPLC-DAD method, the contents of the target compounds were determined by area normalization: the content of the compound N-cyclopropyl-3-n-butyl-3-hydroxy-ligusticum lactam is 91.2%; and the content of the compound N-cyclopropyl-3-n-butyl-3-hydroxy-phthalide lactam is 7.9%.

Example 5: Synthesis of a Mixture of the Compound N-cyclopropyl-3-n-butyl-3-hydroxy-ligusticum Lactam and the Compound N-cyclopropyl-3-n-butyl-3-hydroxy-phthalide Lactam Using *Angelica sinensis* Volatile Oil The Example is to examine the effect of temperature on the product yield and the relative contents of the two compounds. Since ligustilide is unstable, it is prone to be subjected to the aromatization reaction during the heat treatment, reducing the production of N-cyclopropyl-3-n-butyl-3-hydroxy-ligusticum lactam and increasing the production of N-cyclopropyl-3-n-butyl-3-hydroxy-phthalide lactam.

The prepared *Angelica sinensis* volatile oil was pre-separated by column chromatography using petroleum ether and ethyl acetate (3:1, V/V) as eluent. The portion of *Angelica sinensis* volatile oil having a higher content of ligustilide (3.000 g) was dissolved in 60 mL of tetrahydrofuran, and cyclopropylamine (0.684 g, 0.012 mol) was dissolved in 30 mL of tetrahydrofuran. Under mechanical stirring, the solution of cyclopropylamine in tetrahydrofuran was dropwise added to the above solution of *Angelica sinensis* volatile oil in tetrahydrofuran. The water bath was heated to 45° C., and the reaction was carried out at the constant temperature under stirring for 10 h. The tetrahydrofuran and excess cyclopropylamine solution were recycled by rotary evaporation under reduced pressure. 200 mL of petroleum ether was added to the above concentrate, mixed uniformly, left to stand overnight until the synthesized product crystals were precipitated, then filtered by suction, to obtain 2.562 g of crude product (product yield: 85.4%). The crude product was recrystallized from a mixed solvent of petroleum ether and acetone (10:1, V/V), to obtain 2.050 g of crystal product (crystal yield: 80%). Using HPLC-DAD method, the contents of the target compounds were determined by area normalization: the content of the compound N-cyclopropyl-3-n-butyl-3-hydroxy-ligusticum lactam is 70.0%; and the content of the compound N-cyclopropyl-3-n-butyl-3-hydroxy-phthalide lactam is 28.1%.

Example 6: Synthesis of Individual Compounds N-cyclopropyl-3-n-butyl-3-hydroxy-ligusticum Lactam and N-cyclopropyl-3-n-butyl-3-hydroxy-phthalide Lactam Using *Angelica sinensis* Volatile Oil The prepared *Angelica sinensis* volatile oil was pre-separated by column chromatography using petroleum ether and ethyl acetate (3:1, V/V) as eluent. The portion of *Angelica sinensis* volatile oil having a higher content of ligustilide (3.000 g) was dissolved in 60 mL of tetrahydrofuran, and cyclopropylamine (0.684 g, 0.012 mol) was dissolved in 30 mL of tetrahydrofuran. Under mechanical stirring, the solution of cyclopropylamine in tetrahydrofuran was dropwise added to the above solution of *Angelica sinensis* volatile oil in tetrahydrofuran, and the reaction was carried out at room temperature under mechanical stirring for 10 h. The tetrahydrofuran and excess cyclopropylamine solution were recycled by rotary evaporation under reduced pressure. 200 mL of petroleum ether was added to the above concentrate, mixed uniformly, and left to stand overnight until the synthesized product crystals were precipitated, then filtered by suction, to obtain 2.302 g of crude product (product yield: 76.7%).

The crude product was separated and purified by column chromatography using petroleum ether and ethyl acetate (3:1, V/V) as eluent, to obtain three components A, B and C respectively. The obtained component A (0.483 g) was identified as N-cyclopropyl-3-n-butyl-3-hydroxy-phthalide lactam by thin layer chromatography; the obtained component B (0.420 g) was identified as a mixture of the compound N-cyclopropyl-3-n-butyl-3-hydroxy-ligusticum lactam and the compound N-cyclopropyl-3-n-butyl-3-hydroxy-phthalide lactam by thin layer chromatography; and the obtained component C (1.128 g) was identified as the compound N-cyclopropyl-3-n-butyl-3-hydroxy-ligusticum lactam by thin layer chromatography. Using HPLC-DAD method, the contents of the target compounds were determined by area normalization: the content of component A is 99.4%; in component B, the content of the compound N-cyclopropyl-3-n-butyl-3-hydroxy-ligusticum lactam is 66.9%, and the content of the compound N-cyclopropyl-3-n-butyl-3-hydroxy-phthalide lactam is 36.5%; the content of the component C is 99.6%.

Example 7: Synthesis of the Compound N-cyclopropyl-3-n-butyl-3-hydroxy-ligusticum lactam and the Compound N-cyclopropyl-3-n-butyl-3-hydroxyphthalide Lactam Compound Using a Mixture of *Angelica sinensis* and *Ligusticum wallichii* Volatile Oils The prepared *Angelica sinensis* and *Ligusticum wallichii* volatile oil mixture was pre-separated by column chromatography using petroleum ether and ethyl acetate (3:1, V/V) as eluent. The portion of volatile oil mixture having a higher content of ligustilide (3.000 g) was dissolved in 60 mL of tetrahydrofuran, and cyclopropylamine (0.684 g, 0.012 mol) was dissolved in 30 mL of tetrahydrofuran. Under mechanical stirring, the solution of cyclopropylamine in tetrahydrofuran was dropwise added to the above solution of *Angelica sinensis* and *Ligusticum wallichii* volatile oil in tetrahydrofuran, and the reaction was carried out at room temperature under stirring for 6 h. The tetrahydrofuran and excess cyclopropylamine solution were recycled by rotary evaporation under reduced pressure. 200 mL of petroleum ether was added to the above concentrate, mixed uniformly, left to stand overnight at −20° C. until the synthesized product crystals were precipitated, then filtered by suction, to obtain 2.602 g of crude product (product yield: 86.7%). The crude product was recrystallized from a mixed solvent of petroleum ether and acetone (10:1, V/V), to obtain 2.080 g of crystal product (crystal yield: 80%). Using HPLC-DAD method, the contents of the target compounds were determined by area normalization: the content of the compound N-cyclopropyl-3-n-butyl-3-hydroxy-ligusticum lactam is 92.5%; and the content of the compound N-cyclopropyl-3-n-butyl-3-hydroxy-phthalide lactam is 7.5% (as shown in FIG. 15).

Example 8: Study on the Neuroprotection Effects of Phthalide Derivatives

1. Materials: PC12 cells (Shanghai Institute of Cell Sciences, Chinese Academy of Sciences); phthalide derivatives (prepared by above Examples), high-sugar culture medium (DMEM, Nanjing Kaiji Biotechnology Development Co., Ltd.); dimethyl sulfoxide (DMSO, Sigma); fetal bovine serum (Gibco, Thermo Fisher Scientific Co., Ltd.); $H_2O_2$ (Nanjing Chemical Reagent Co., Ltd.); Thiazolyl Blue (MTT, Nanjing Shengxing Biotechnology Co., Ltd.), microplate reader (Bio-rad, U.S.A.).

2. Method: PC12 cells were cultured as follows. PC12 cells were inoculated into the high-glucose DMEM medium containing 10% fetal bovine serum, penicillin 100 U mL$^{-1}$, and streptomycin 100 μg mL$^{-1}$, and cultured in the cell incubator at 37° C. under 5% $CO_2$. The medium was changed every other day. The cells were routinely trypsinized and passaged. The cells were used for experiments when they reached 70-80% confluence.

3. Effects of phthalide and its derivatives on the proliferation of PC12 cells: PC12 cells in the logarithmic growth phase were inoculated into a 96-well cell culture plate at a density of 1×10$^4$ cells/well. After 24 hours of incubation, 100 μl solution of phthalide and its derivatives was added, so that the final concentrations are 1.25, 2.5, 5.0, 10, 20, 40, 80, and 160 μM, respectively. After another 24 hours of incubation, 100 μl of MTT (5 mg mL$^{-1}$) was added, and incubated for 4 h. Then 150 μl of DMSO was added and shaked for 10 min. The wavelength of 490 nm was selected to detect the absorbance (A) value of each well.

Cell viability (%)($A_{experimental\ group} - A_{blank\ group}$)/ ($A_{control\ group} - A_{blank\ group}$)×100%.

The results showed that ligustilide, ligustilide derivatives, n-butenylphthalide, n-butenylphthalide derivatives of at least 200 μM could inhibit the growth of PC12 cells.

4. Oxidative damage modeling: PC12 cells in the logarithmic growth phase were inoculated into a 96-well cell culture plate at a density of 5×10$^3$ cells/well. $H_2O_2$ was added at different concentrations, and cultured for 4 h. MTT was added according to the above MTT assay, and A value of each well was measured. The $H_2O_2$ concentration at which the cell viability was reduced by 50% was finally selected as the modelling concentration.

The results showed that 250 μM of $H_2O_2$ could inhibit the growth of 50% of PC12 cells. Therefore, 250 μM was selected as the induction concentration of nerve cell oxidative damage.

5. Grouping and drug treatment: The experimental groups was divided into the normal blank control group, the $H_2O_2$ model group (250 μM), concentration groups (2.5 μM, 5.0 μM, 10 μM, 25 μM, 50 μM) for phthalides and their derivatives, and the positive control group (butylphthalide). Each group for phthalides and their derivatives as well as the positive control group were added with 250 μM $H_2O_2$, respectively. In the experiment, the solutions of phthalides and their derivatives were first added respectively, so that the final concentrations reached the corresponding values. After 4 h, $H_2O_2$ was added, and MTT was added after 24 h. The A value was measured to calculate the cell viability.

The study results are shown in FIG. 16. "**" in the figure indicates a statistically relatively significant difference (P<0.01%) between the result and the positive control, and "*" in the figure indicates a statistically significant difference (P<0.05%) between the result and the positive control. It can be seen from the figure that the ligustilide derivative (a racemic mixture) prepared according to Example 1 has the strongest protective effect on PC12 nerve cells against hydrogen peroxide. At the minimum experimental concentration of 2.5 μM, the cell viability can be improved by 80%. Compared to 52% in the model group and 68% in the drug positive control group, this compound can significantly protect PC12 cells from the oxidative damage of hydrogen peroxide. When the concentration of the ligustilide derivative was 10 μM, the cell viability was the highest and reached 95%. Secondly, the protective activity against the oxidative damage to nerve cells of ligustilide is stronger than that of n-butenylphthalide. Ligustilide and the n-butenylphthalide derivative prepared according to Example 2 (a racemic mixture) have almost the same protective effects against the oxidative damage to nerve cells.

Example 9: Study on the Inhibitory Effects of Phthalide Derivatives on the Cerebral Infarction in the Acute Ischemic Stroke 1. Experimental animals: Four-week-old Wistar male rats (230-250 g), provided by Lanzhou Veterinary Research Institute, Chinese Academy of Agricultural Sciences.

2. Preparation of animal models: 75 rats purchased according to the standards were strictly raised at the clean grade according to the reference method (Xiaomei Wu, Zhongming Qian, Li Zhu, Fang Du, Wingho Yung, Qi Gong and Ya Ke, Neuroprotective effect of ligustilide against ischaemia-reperfusion injury via up-regulation of erythropoietin and down-regulation of RTP801, British J Pharm. 2011, 164, 332-343). MCAO model (Middle Cerebral Artery Obstruction in rats) was established through suture-occlusion, and the rats were intraperitoneally injected with 10% chloral hydrate at a dosage of 400 mg/kg for anesthetization. The rats were fixed with supine position method to expose the neck. It was shaved and the skin was cleaned for skin incision. Under gentle operations, the main blood vessels such as left common carotid artery, arteria carotis interna, and arteria carotis externa were separated. The arteria carotis externa was selected to be ligated and disconnected, to avoid the bleeding of the common carotid artery. The common carotid artery was temporarily clamped with an arterial clip. A small opening was cut at the end of arteria carotis extern, and used for the placement of the suture-occlusion. The round head of the prepared suture-occlusion was held by the ophthalmic tweezer and gently inserted, with a controlled depth of about 1.8-2.0 cm. The incision was sutured conventionally. After 0.5 h of cerebral ischemia, the suture-occlusion was removed to restore the blood supply. At a certain time after administration, the rats were sacrificed. The brain tissue was stained with 0.5% 2,3,5-triphenyltetrazolium chloride (TCC), and the cerebral infarction area was scanned and calculated, wherein the normal tissue was stained in red and the infarcted tissue was stained in white.

3. Animal grouping: The animals were grouped as follows: the model group (acute ischemia and hypoxia pathological model, administrated with an equal dosage of physiological saline containing 8% Tween-80), the sham operation group (not administrated, as the negative control, administrated with an equal dosage of physiological saline containing 8% Tween-80), the prevention group (administrated 3 days in advance), and treatment group (administrated for 3 days after the blood supply was restored from embolism).

4. Method of administration: The ligustilide derivative (phthalide derivative prepared according to Example 1: the content of N-cyclopropyl-3-n-butyl-3-hydroxy-ligusticum lactam reaches 98% (through HPLC-DAD area normalization); dissolved in a physiological saline containing 8% Tween-80) was intraperitoneally injected at a dosage of 40 mg/Kg.

5. Results: It can be seen from FIG. 17 that after the acute cerebral ischemia model was established in rats, the administration of N-cyclopropyl-3-n-butyl-3-hydroxy-ligusticum lactam can effectively prevent the occurrence of cerebral infarction as compared to the model group (A group), and thus has a good therapeutic effect (B group). However, due to the vasodilatation activity of the compound, the common carotid artery in the rats of the prevention group (C group) may be dilated, leading to non-parallel model animals, making it easy to cause the deaths of model animals and resulting in relatively weak anti-embolic effects in the survived animals in this group. A. Negative model control, infarct area: 30.57%; B. N-cyclopropyl-3-n-butyl-3-hydroxy-ligusticum lactam treatment group, (dosed for 3 days after modeling, 40 mg/kg, intraperitoneal injection), left side infarct area: 4%, complete recanalization in the middle portion (infarct area 0%), a negative value for the right side as calculated according to the edema removal method; C. N-cyclopropyl-3-n-butyl-3-hydroxy-ligusticum lactam prevention group, (pre-dosed for 3 days; modeling; dosed for another 3 days; 440 mg/kg, intraperitoneal injection), infarct area: 22%.

Example 10: Study on In Vivo Pharmacokinetics of Phthalide Derivatives in Rats

1. Experimental Method 1.1 Establishment of the quantitative detection method for the compound. The HPLC-DAD standard curve method is used to determine the detection limit (LOD), the quantification limit (LOQ) and the linear range of the method.

Certain amounts of N-cyclopropyl-3-n-butyl-3-hydroxy-ligusticum lactam and N-cyclopropyl-3-n-butyl-3-hydroxy-phthalide lactam standards were accurately weighed respectively, and dissolved and diluted in the methanol to obtain 2.0 mg/mL of standard stock solutions. Certain standard stock solutions were accurately weighed and mixed respectively, and diluted with methanol to 0.1953, 0.395, 0.7813, 1.5625, 3.1250, 6.2500, 12.500, 25.0000, 50.0000, and 500.0 μg/mL. 20 uL of each sample was analyzed by HPLC system, to sequentially determine N-cyclopropyl-3-n-butyl-3-hydroxy-ligusticum lactam and N-cyclopropyl-3-n-butyl-3-hydroxy-phthalide lactam. The peak area (A) was linearly regressed with the concentration C (g/mL), to obtain the regression equation and linear range, detection limit (LOD), and quantification limit (LOQ).

TABLE 1

The detection items, quantification limit, and linear range of HPLC-DAD detection method

| Detection Items | N-cyclopropyl-3-n-butyl-3-hydroxy-ligusticum lactam | N-cyclopropyl-3-n-butyl-3-hydroxy-phthalide lactam |
|---|---|---|
| LOD (μg/mL) | 0.0488 | 0.0976 |
| LOQ (μg/mL) | 0.1953 | 0.3906 |
| Linear range (μg/mL) | 0.3906-960.0 | 0.7813-480.0 |
| Linear equation | Y = 9.6228x + 8.9893 | Y = 16.438x + 10.669 |
| Correlation coefficient $R^2$ | 0.9981 | 0.9995 |

1.2 Preparation method for test sample: The compound prepared according to Example 7 (the content of N-cyclopropyl-3-n-butyl-3-hydroxy-ligusticum lactam is 92.5%; and the content of the compound N-cyclopropyl-3-n-butyl-3-hydroxy-phthalide lactam is 7.5%) was prepared into the raw stock solution at a concentration of 15 mg/mL by 10% ethanol, 20% Tween 80, and 70% physiological saline. The rats were dosed based on the body weights, with a dosage of 90 mg/Kg by oral administration (by gavage) and a dosage of 40 mg/Kg by intravenous injection.

1.3 Pretreatment method for plasma sample: 0.5 mL of rat whole blood was taken and placed in a 1.5 mL centrifuge tube with 20 uL sodium heparin therein, and centrifuged at a high rotation rate of $4 \times 10^3$ r·min$^{-1}$ for 5 min. 200 μL of plasma was taken and 800 μL of dichloromethane was added. The mixture was vortexed and centrifuged for 10 min at a rotation rate of $1 \times 10^5$ r·min$^{-1}$. The lower layer solution was separate and blown to dryness with nitrogen gas at room temperature, and then reconstituted with 300 μL of methanol. The solution was eluted, filtered, and dried to dryness with nitrogen. After adding 30 μL of methanol, the solution was centrifuged, and 20 μL of the supernatant was used to determine the peak areas by HPLC.

1.4 Determination of pharmacokinetic parameters of phthalide derivatives in rats. Twelve male Wistar rats were randomly divided into two groups, wherein 6 rats were administrated with 40 mg/kg of phthalide derivative (the intravenous injection group (i.v.)). At 0 (pre-dose), 0.167, 0.333, 0.5, 1, 2, 3, 4, and 6 hours after administration, about 500 μL of blood was collected from the *Angulus oculis*, respectively, and 200 μL of plasma was frozen after anticoagulation treatment and centrifugation. 6 rats in the gavage administration (po) group were administrated by 90 mg/kg of phthalide derivative. At 0 (pre-dose), 0.5, 1, 2, 3, 4, 6, 8, 10, and 12 h after administration, about 500 μL of blood was collected from the *Angulus oculis*, respectively, and 200 μL of plasma was frozen after anticoagulation treatment and centrifugation. The plasma samples were warmed to the room temperature before pretreatment, and 20 μL of the sample solutions were analyzed by liquid chromatography. The blood drug concentration at each time point was calculated according to the standard curve. The dose-time curve was fitted using DAS2.0 software and the pharmacokinetic parameters were calculated. FIGS. 18 and 19 show the dose-time curves by gavage administration and intravenous injection, respectively.

TABLE 2

Pharmacokinetic parameters of the compound N-cyclopropyl-3-n-butyl-3-hydroxy-ligusticum lactam (ligustilide cyclopropiolactam) and the compound N-cyclopropyl-3-n-butyl-3-hydroxy-phthalide lactam (n-butylcyclopropiolactam) when administrated by gavage and intravenous injection.

| Ligustilide cyclopropiolactam (po) | | | n-butyl cyclopropiolactam (po) | | | Ligustilide cyclopropiolactam (iv) | | |
|---|---|---|---|---|---|---|---|---|
| model parameters | Unit | No2 | model parameters | Unit | No1 | model parameters | Unit | No1 |
| t1/2α | h | 0.122 | t1/2α | h | 0.204 | t1/2α | h | 0.088 |
| t1/2β | h | 1.478 | t1/2β | h | 3.029 | t1/2β | h | 3.213 |
| t1/2γ | h | 2.643 | t1/2γ | h | 3.513 | V1 | L/kg | 3739.124 |
| V1 | L/kg | 722.758 | V1 | L/kg | 529.323 | V2 | L/kg | 17537.504 |
| V2 | L/kg | 1701.61 | V2 | L/kg | 1478.868 | CL1 | L/h/kg | 5445.044 |
| V3 | L/kg | 240.115 | V3 | L/kg | −302.598 | CL2 | L/h/kg | 20518.475 |
| CL1 | L/h/kg | 2719.904 | CL1 | L/h/kg | 893.769 | AUC(0-t) | ug/L * h | 6.017 |
| CL2 | L/h/kg | 1163.858 | CL2 | L/h/kg | 802.825 | AUC(0-∞) | ug/L* h | 12.098 |
| CL3 | L/h/kg | 65.258 | CL3 | L/h/kg | −50.58 | R_AUC(t/∞) | % | 49.7 |
| AUC(0-t) | ug/L * h | 35.347 | AUC(0-t) | ug/L * h | 23.222 | K10 | 1/h | 1.456 |
| AUC(0-∞) | ug/L * h | 37.065 | AUC(0-∞) | ug/L * h | 25.83 | K12 | 1/h | 5.488 |
| R_AUC(t/∞) | % | 95.4 | R_AUC(t/∞) | % | 89.9 | K21 | 1/h | 1.17 |
| K10 | 1/h | 3.763 | K10 | 1/h | 1.689 | | | |
| K12 | 1/h | 1.61 | K12 | 1/h | 1.517 | | | |
| K21 | 1/h | 0.684 | K21 | 1/h | 0.543 | | | |
| K31 | 1/h | 0.272 | K31 | 1/h | 0.167 | | | |
| K13 | 1/h | 0.09 | K13 | 1/h | −0.096 | | | |
| Ka | 1/h | 4.021 | Ka | 1/h | 2.425 | | | |
| T1/2ka | 1/h | 0.172 | T1/2ka | 1/h | 0.286 | | | |
| Tmax | h | 1.196 | Tmax | h | 1.768 | | | |
| Cmax | ug/L | 8.82 | Cmax | ug/L | 4.215 | | | |

The provision of the above Examples is only for the purpose of facilitating the understanding of the method and inventive gist of the present invention. It should be noted that, for those of ordinary skill in the art, various improvements and modifications could also be made to the present invention without departing from the spirit of the invention. These improvements and modifications also fall within the protection scope of the claims of the present invention.

What is claimed is:

1. A phthalide derivative of Formula I or Formula II, an optical isomer or pharmaceutically acceptable salt thereof, or their mixtures

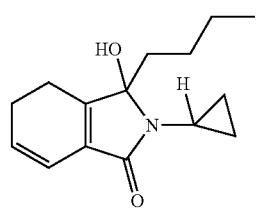

Formula I

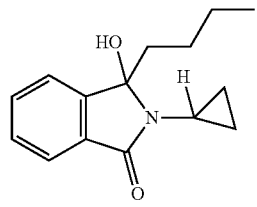

Formula II

2. The phthalide derivative according to claim 1, which is N-cyclopropyl-3-n-butyl-3-S-hydroxy-ligusticum lactam, N-cyclopropyl-3-n-butyl-3-R-hydroxy-ligusticum lactam, N-cyclopropyl-3-n-butyl-3-S-hydroxy-phthalide lactam, or N-cyclopropyl-3-n-butyl-3-R-hydroxy-phthalide lactam.

3. A method for preparing a phthalide derivative of Formula I,

Formula I

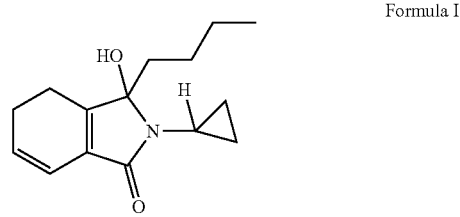 [SMILES: CCCCC1(O)C2=C(C=CCC2)C(=O)N1C1CC1]

comprising reacting ligustilide with cyclopropylamine in an organic solvent, wherein the original lactone structure fragment in the phthalide compound is replaced by a lactam group and the C3-position is substituted by hydroxyl group,

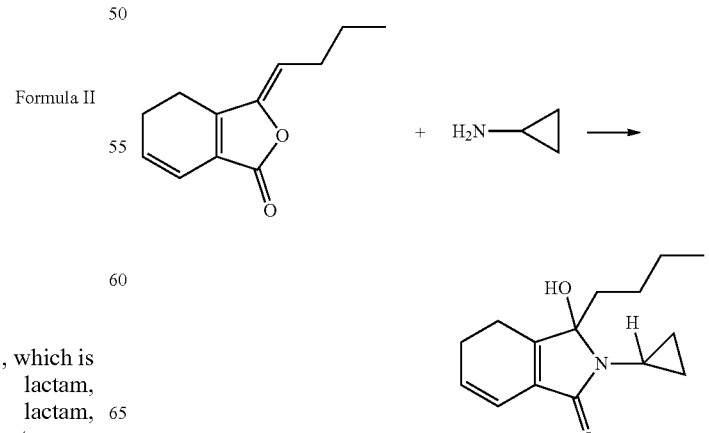

4. The method according to claim 3, wherein
1) the phthalide compound is a dihydrobenzene ring type;
2) the reaction is carried out at −20° C. to 60° C., and optionally carried out under stirring;
3) the organic solvent is a nonpolar organic solvent, selected from cyclohexane, petroleum ether, tetrahydrofuran, and diethyl ether; and/or
4) the method also comprises a step of chiral resolution of enantiomers, by chiral chromatography or chiral recrystallization.

5. The method according to claim 3, wherein the molar ratio of the phthalide compound to cyclopropylamine is from 1:1 to 1.2.

6. The method according to claim 3, further comprising a step of recycling the organic solvent under reduced pressure and recrystallizing to obtain the target product, wherein the solvent used for the recrystallization is one or two of petroleum ether, ethyl acetate, acetone, and diethyl ether.

7. The method according to claim 3, comprising adding and dissolving the phthalide compound in the organic solvent, with the temperature controlled at −20° C. to 60° C., and adding a reaction solution of cyclopropylamine dissolved in an organic solvent, with the temperature controlled at −20° C. to 60° C., stirring and reacting for 1-24 hours, recycling the organic solvent under reduced pressure, and recrystallizing to obtain the target product.

8. A phthalide derivative, prepared by the method according to claim 3, an optical isomer or pharmaceutically acceptable salt thereof, or their mixtures.

9. A method of anti-oxidation or treatment of the following diseases: cardiovascular and cerebrovascular diseases, depression, Alzheimer's disease, (neuro-)inflammatory diseases, pain, neuronal cell damage, ischemia-reperfusion injury, cerebral infarction, cognitive impairment, or brain damage, comprising administering a therapeutically effective amount of the phthalide derivative of Formula I or Formula II according to claim 1, an optical isomer or pharmaceutically acceptable salt thereof, or their mixtures to a subject in need of the anti-oxidation or treatment.

10. The method according to claim 9, wherein a mixture of the compound of Formula I and the compound of Formula II as active ingredient is administered, wherein the mass percentage of the compound of Formula I in the mixture is 1-1000%.

* * * * *